(12) United States Patent
Kersh et al.

(10) Patent No.: US 12,186,185 B2
(45) Date of Patent: *Jan. 7, 2025

(54) PROSTHETIC HEART VALVE

(71) Applicant: Edwards Lifesciences Corporation, Irvine, CA (US)

(72) Inventors: Dikla Kersh, Karkur (IL); Michael Bukin, Pardes Hanna (IL); Tamir S. Levi, Zikhron Yaakov (IL); Noam Nir, Pardes-Hanna (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 17/863,195

(22) Filed: Jul. 12, 2022

(65) Prior Publication Data

US 2022/0346949 A1 Nov. 3, 2022

Related U.S. Application Data

(63) Continuation of application No. 16/941,776, filed on Jul. 29, 2020, now Pat. No. 11,399,932, which is a
(Continued)

(51) Int. Cl.
*A61F 2/24* (2006.01)

(52) U.S. Cl.
CPC .... *A61F 2/2418* (2013.01); *A61F 2210/0014* (2013.01); *A61F 2220/0008* (2013.01); *A61F 2220/0075* (2013.01); *A61F 2250/001* (2013.01)

(58) Field of Classification Search
CPC .................................... A61F 2/2418
See application file for complete search history.

(56) References Cited

U.S. PATENT DOCUMENTS

| 30,912 A | 12/1860 | Hancock |
| 3,409,013 A | 11/1968 | Berry |
| (Continued) | | |

FOREIGN PATENT DOCUMENTS

| CN | 108125732 A | 6/2018 |
| DE | 0144167 C | 9/1903 |
| (Continued) | | |

OTHER PUBLICATIONS

H.R. Andersen, et al. "Transluminal Implanation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suba Ganesan
(74) *Attorney, Agent, or Firm* — Klarquist Sparkman, LLP; Sean Seung Kyu Kim

(57) ABSTRACT

A prosthetic valve assembly includes a radially expandable and compressible annular frame. The frame includes a plurality of interconnected struts, which include a plurality of inner struts and a plurality of outer struts. The inner struts overlap adjacent outer struts at a plurality of pivot joints. Radial expansion or compression of the annular frame causes the inner struts to pivot relative to the outer struts at the pivot joints. The assembly also includes a valvular structure having a plurality of leaflets, each leaflet having a cusp edge portion. The assembly further includes one or more leaflet-supporting cords, each having a plurality of anchoring portions and a plurality of suspended portions, each suspended portion extending between two adjacent anchoring portions. The anchoring portions are affixed to respective anchoring features of the frame adjacent the pivot joints. The cusp edge portions of the leaflets are connected to the suspended portions.

19 Claims, 16 Drawing Sheets

Related U.S. Application Data continuation of application No. PCT/US2020/024559, filed on Mar. 25, 2020.

(60) Provisional application No. 62/854,702, filed on May 30, 2019, provisional application No. 62/823,905, filed on Mar. 26, 2019.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |

(56) References Cited

U.S. PATENT DOCUMENTS

| | | |
|---|---|---|
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075724 A1 | 4/2005 | Svanidze et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0195134 A1 | 8/2006 | Crittenden |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1* | 6/2013 | Cartledge ............ A61F 2/2439 623/1.2 |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0005771 A1 | 1/2014 | Braido et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2017/0135813 A1* | 5/2017 | Braido ................ A61F 2/2412 |
| 2018/0028310 A1 | 2/2018 | Gurovich et al. |
| 2018/0078367 A1* | 3/2018 | Saar .................... A61F 2/2412 |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0046315 A1 | 2/2019 | Gao et al. |
| 2019/0069995 A1 | 3/2019 | Levi et al. |
| 2019/0159894 A1 | 5/2019 | Levi et al. |

(56) References Cited

U.S. PATENT DOCUMENTS

| | | |
|---|---|---|
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 2246526 C3 | 7/1981 |
| DE | 19532846 A1 | 3/1997 |
| DE | 19907646 A1 | 8/2000 |
| DE | 10049813 C1 | 4/2002 |
| DE | 19546692 C2 | 11/2002 |
| DE | 10049812 B4 | 6/2004 |
| DE | 19857887 B4 | 5/2005 |
| DE | 10049815 B4 | 10/2005 |
| DE | 10049814 B4 | 10/2006 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 B1 | 1/2003 |
| GB | 2056023 B | 8/1983 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006032051 A2 | 3/2006 |
| WO | 2006034008 A2 | 3/2006 |
| WO | 2006014233 A3 | 9/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2008005405 A2 | 1/2008 |
| WO | 2007097983 A3 | 3/2008 |
| WO | 2008035337 A2 | 3/2008 |
| WO | 2008015257 A3 | 4/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A3 | 9/2009 |
| WO | 2009116041 A2 | 9/2009 |
| WO | 2009094188 A3 | 10/2009 |
| WO | 2010011699 A3 | 5/2010 |
| WO | 2010121076 A2 | 10/2010 |
| WO | 2009149462 A8 | 1/2011 |
| WO | 2013106585 A1 | 7/2013 |
| WO | 2015085218 A8 | 7/2016 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

\* cited by examiner

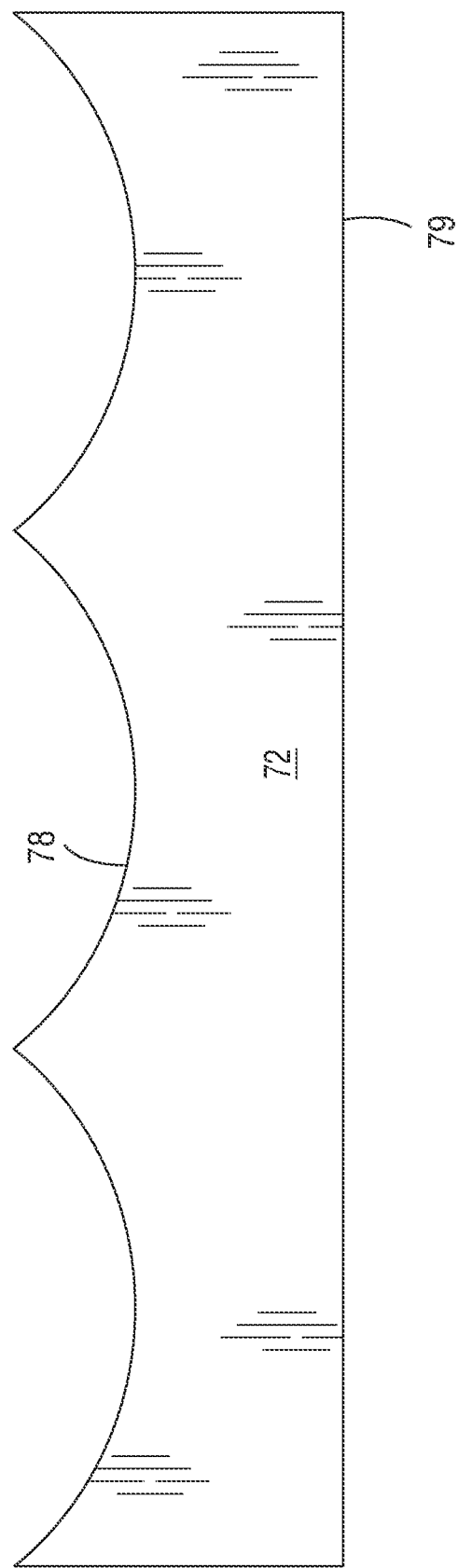

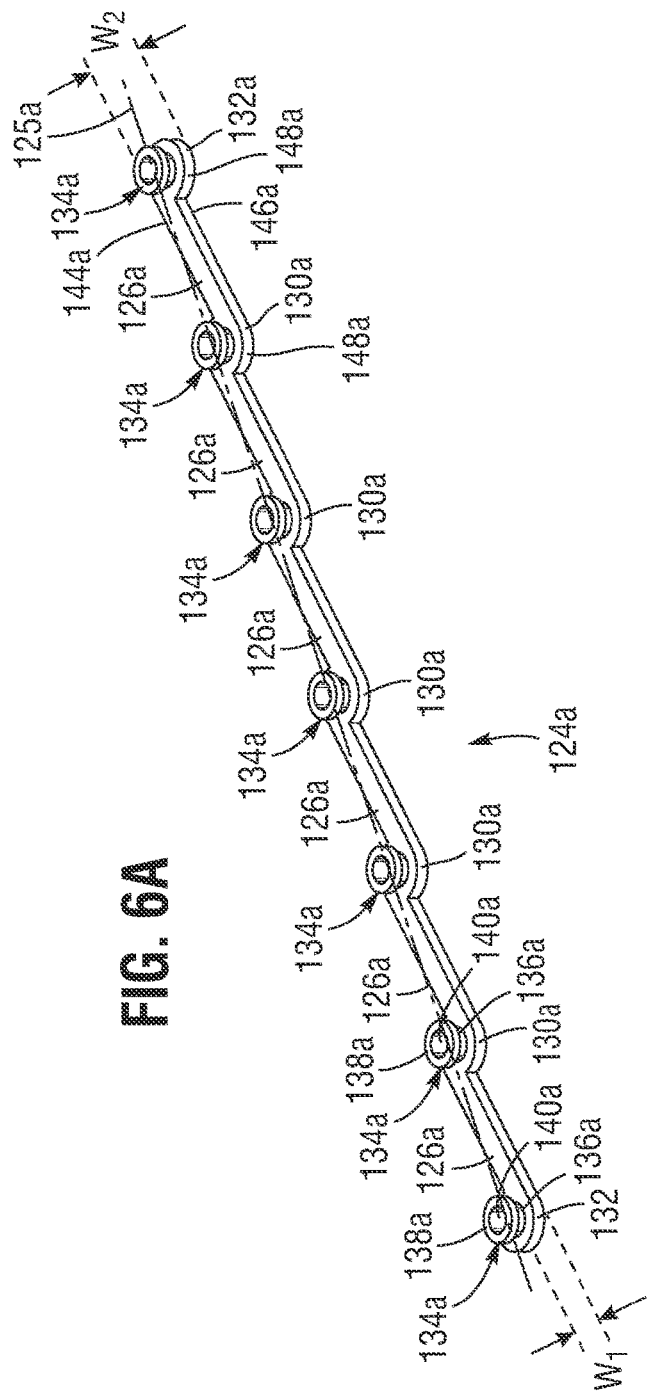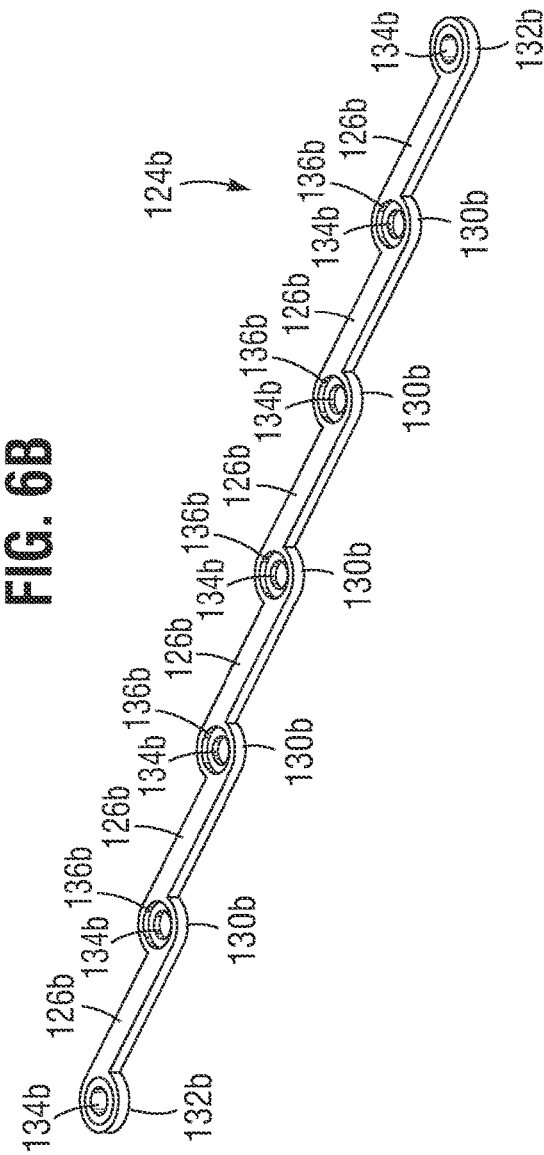

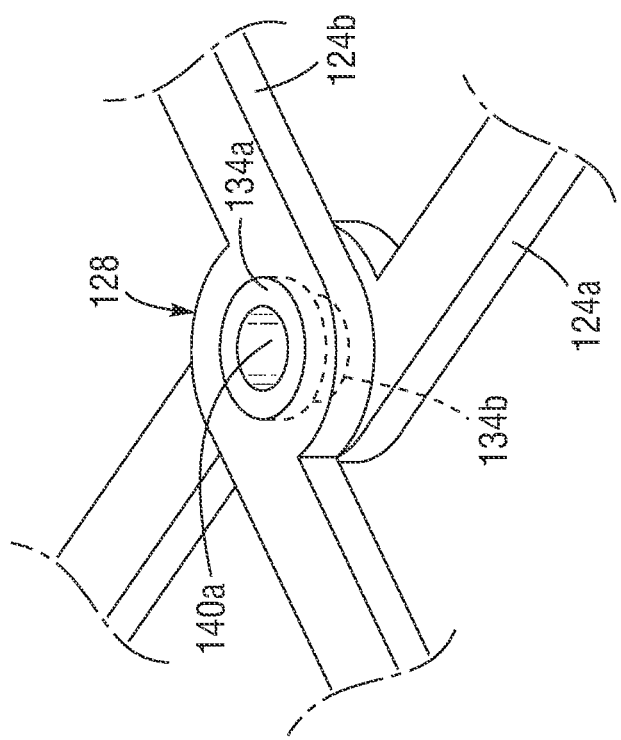

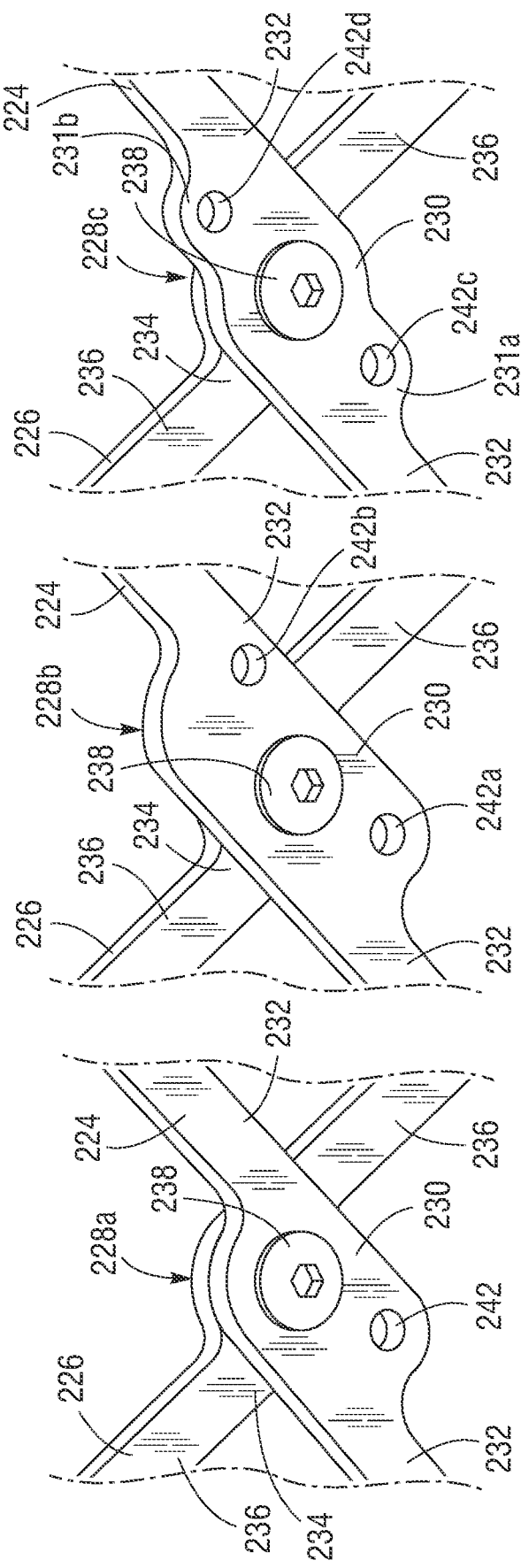

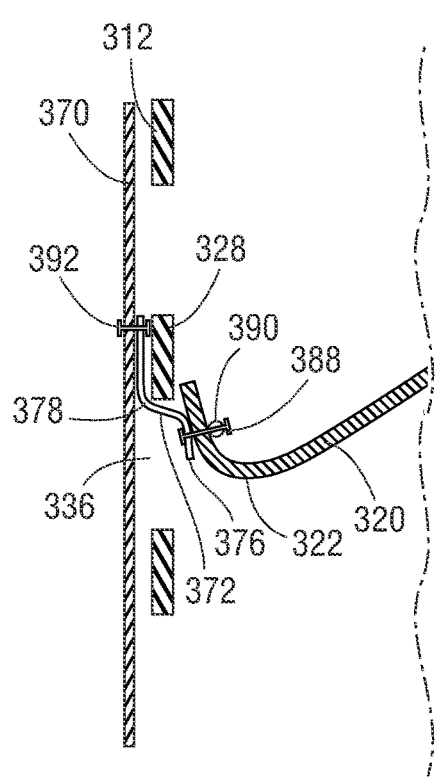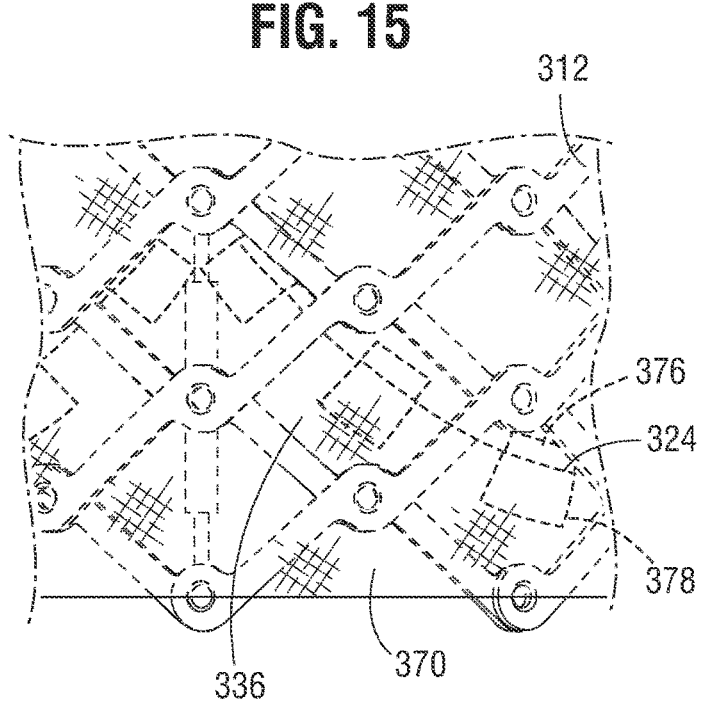

PROSTHETIC HEART VALVE

CROSS-REFERENCE TO RELATED APPLICATIONS

This application is a continuation of U.S. patent application Ser. No. 16/941,776, filed Jul. 29, 2020, which is a continuation of PCT Patent Application No. PCT/US2020/024559, filed Mar. 25, 2020, which claims the benefit of U.S. Provisional Application No. 62/823,905, filed Mar. 26, 2019, and U.S. Provisional Application No. 62/854,702, filed May 30, 2019, all of which applications are incorporated herein by reference.

FIELD

The present disclosure relates to implantable, mechanically expandable prosthetic devices, such as prosthetic heart valves, and to methods and assemblies for providing collapsible frames for, including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering attention. In one technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position. Despite the recent advancements in percutaneous valve technology, there remains a need for improved transcatheter heart valves and delivery devices for such valves.

SUMMARY

Described herein are examples of prosthetic valves and related methods of assembling the same. Prosthetic valves disclosed herein can be implanted within any of the native valves of the heart (e.g., the aortic, mitral, tricuspid and pulmonary valves). In some embodiments, the prosthetic valve can be delivered through the vasculature and implanted to the heart of a patient by using a delivery apparatus.

Certain embodiments of the disclosure also concern a prosthetic valve assembly having a radially expandable and compressible annular frame, a valvular structure, and one or more leaflet-supporting cords. The frame can include a plurality of inner struts and a plurality of outer struts. The inner struts can overlap adjacent outer struts at a plurality of pivot joints and radial expansion or compression of the annular frame can cause the inner struts to pivot relative to the outer struts at the pivot joints. The valvular structure can include a plurality of leaflets configured to permit the flow of blood from an inflow end to an outflow end of the prosthetic valve assembly and block the flow of blood from the outflow end to the inflow end of the prosthetic valve assembly, each leaflet having a cusp edge portion. Each leaflet-supporting cord can include a plurality of anchoring portions and a plurality of suspended portions. Each suspended portion can extend between two adjacent anchoring portions. The anchoring portions can be affixed to respective anchoring features of the frame adjacent the pivot joints. The cusp edge portions of the leaflets can be connected to the suspended portions.

In some embodiments, each of the one or more leaflet-supporting cords can include at least a first segment that extends diagonally along one of the inner or outer struts and at least a second segment that extends diagonally along another one of the inner or outer struts.

In some embodiments, the one or more leaflet-supporting cords can include a single continuous cord connected to each of the leaflets.

In some embodiments, the one or more leaflet-supporting cords can include a plurality of leaflet-supporting cords, each of which is connected to one of the leaflets.

In some embodiments, the anchoring features can include openings in one or both of the inner and outer struts and the anchoring portions of the one or more leaflet-supporting cords can extend through the openings.

In some embodiments, the anchoring features can include notches in one or both of the inner and outer struts and the anchoring portions of the one or more leaflet-supporting cords can extend through the notches.

In some embodiments, each anchoring feature can be located on an intermediate strut segment which connects a first liner strut segment with a second liner strut segment. The first and second linear strut segments can be offset to each other and located on opposite side of the intermediate strut segment.

In some embodiments, each of the anchoring portions of the one or more leaflet-supporting cords can be affixed to a pair of first and second anchoring features of the frame adjacent a respective pivot joint.

In some embodiments, the first and second anchoring features of each pair can be located at diametrically opposing locations of the respective pivot joint.

In some embodiments, the first and second anchoring features of each pair can be on the same strut, which can be one of the inner struts or one of the outer struts.

In some embodiments, one of the first and second anchoring features of each pair can be on one of the inner struts and the other of the first and second anchoring features of each pair can be on one of the outer struts.

In some embodiments, each of the anchoring portions can include one or more loops of the cord that extends through at least one anchoring feature and around a pair of inner and outer struts at a respective pivot joint.

In some embodiments, the one or more loops of each anchoring portion can include a self-locking knot.

In some embodiments, the prosthetic valve assembly can further include an annular inner skirt covering at least a portion of an inner surface of the frame. The inner skirt can be attached to the leaflets.

In some embodiments, the inner skirt can include an undulating, curved support portion and a plurality of flaps extending from the support portion. The support portion can be sutured to the cusp edge portions of the leaflets and the plurality of flaps can be separated by a plurality of slits.

In some embodiments, the plurality of flaps can extend outside of the frame through adjacent open cells of the frame.

In some embodiments, each flap extending outside of the frame can overlap with an adjacent pivot joint of the frame.

In some embodiments, the plurality of flaps extending outside of the frame can be attached to an outer skirt of the prosthetic valve.

Some embodiments of the disclosure concerns a prosthetic valve assembly including a radially expandable and compressible annular frame, a valvular structure, an inner skirt covering at least a portion of an inner surface of the frame, and an outer skirt covering at least a portion of an outer surface of the frame. The frame can include a plurality of inner struts and a plurality of outer struts. The inner struts can overlap adjacent outer struts at a plurality of pivot joints and radial expansion or compression of the annular frame can cause the inner struts to pivot relative to the outer struts at the pivot joints. The valvular structure can include a plurality of leaflets configured to permit the flow of blood from an inflow end to an outflow end of the prosthetic valve assembly and block the flow of blood from the outflow end to the inflow end of the prosthetic valve assembly, each leaflet having a cusp edge portion. The inner skirt can include a support portion and a plurality of flaps extending from the support portion. The plurality of flaps can be separated by a plurality of slits and the support portion can be attached to the cusp edge portions of the leaflets. The plurality of flaps can extend through adjacent open cells of the frame and be attached to the outer skirt.

In some embodiments, each flap can overlap an adjacent pivot joint of the frame.

In some embodiments, the prosthetic valve assembly can further include one or more leaflet-supporting cords. Each leaflet-supporting cord can have a plurality of anchoring portions and a plurality of suspended portions. Each suspended portion can extend between two adjacent anchoring portions. The anchoring portions can be affixed to respective anchoring features of the frame adjacent the pivot joints. The cusp edge portions of the leaflets can be connected to the suspended portions.

In some embodiments, each of the one or more leaflet-supporting cords can include at least a first segment that extends diagonally along one of the inner or outer struts and at least a second segment that extends diagonally along another one of the inner or outer struts.

In some embodiments, the one or more leaflet-supporting cords can include a single continuous cord connected to each of the leaflets.

In some embodiments, the one or more leaflet-supporting cords can include a plurality of leaflet-supporting cords, each of which is connected to one of the leaflets.

In some embodiments, the anchoring features can include openings in one or both of the inner and outer struts and the anchoring portions of the one or more leaflet-supporting cords can extend through the openings.

In some embodiments, the anchoring features can include notches in one or both of the inner and outer struts and the anchoring portions of the one or more leaflet-supporting cords can extend through the notches.

In some embodiments, each anchoring feature can be located on an intermediate strut segment. The intermediate strut segment can connect a first liner strut segment with a second liner strut segment. The first and second linear strut segments can be offset to each other and located on opposite side of the intermediate strut segment.

In some embodiments, each of the anchoring portions of the one or more leaflet-supporting cords can be affixed to a pair of first and second anchoring features of the frame adjacent a respective pivot joint.

In some embodiments, the first and second anchoring features of each pair can be located at diametrically opposing locations of the respective pivot joint.

In some embodiments, the first and second anchoring features of each pair can be on the same strut, which can be one of the inner struts or one of the outer struts.

In some embodiments, one of the first and second anchoring features of each pair can be on one of the inner struts and the other of the first and second anchoring features of each pair can be on one of the outer struts.

In some embodiments, each of the anchoring portions can include one or more loops of the cord that extends through at least one anchoring feature and around a pair of inner and outer struts at a respective pivot joint.

In some embodiments, the one or more loops of each anchoring portion can include a self-locking knot.

Some embodiments of the disclosure also concern a method of assembling a prosthetic valve. The method can include forming an annular frame by connecting a plurality of inner struts with a plurality of outer struts at a plurality of pivot joints. The plurality of inner struts can be configured to pivot relative to the plurality of outer struts at the plurality of pivot joints during radial expansion or compression of the frame. The method can further include attaching one or more leaflet-support cords to the frame such that each cord extends along one of inner or outer struts at spaced apart locations and attaching a plurality of leaflets to the one or more leaflet-support cords.

In some embodiments, each of the one or more leaflet-supporting cords can include at least a first segment and a second segment. Attaching the one or more leaflet-supporting cords to the frame can include extending the first segment diagonally along one of the inner or outer struts and extending the second segment diagonally along another one of the inner or outer struts.

In some embodiments, the one or more leaflet-supporting cords can include a single continuous cord. Attaching the plurality of leaflets to the one or more leaflet-support cords can include attaching the plurality of leaflets to the single continuous cord.

In some embodiments, the one or more leaflet-supporting cords can include a plurality of leaflet-supporting cords. Attaching the plurality of leaflets to the one or more leaflet-support cords can include connecting each of the leaflet-supporting cords to a respective leaflet.

In some embodiments, each of the leaflet-supporting cords can include a plurality of anchoring portions and a plurality of suspended portions. Each suspended portion can extend between two adjacent anchoring portions. Attaching the one or more leaflet-supporting cords to the frame can include affixing the anchoring portions to respective anchoring features of the frame adjacent the pivot joints.

In some embodiments, affixing the anchoring portions to respective anchoring features of the frame can include extending the one or more leaflet-supporting cords through openings located in one or both of the inner and outer struts.

In some embodiments, affixing the anchoring portions to respective anchoring features of the frame can include extending the one or more leaflet-supporting cords through notches located in one or both of the inner and outer struts.

In some embodiments, affixing the anchoring portions to respective anchoring features of the frame can include affixing each of the anchoring portion to a pair of first and second anchoring features of the frame located at diametrically opposing locations of a respective pivot joint.

In some embodiments, affixing the anchoring portions to respective anchoring features of the frame can include forming one or more loops at a respective pivot joint by extending the corresponding leaflet-support cord through at least one anchoring feature and around a pair of inner and outer struts at the respective pivot joint.

In some embodiments, affixing the anchoring portions to respective anchoring features of the frame can include forming a self-locking knot at the one or more loops.

In some embodiments, the method can further include attaching the plurality of leaflets to an inner skirt of the prosthetic valve. The inner skirt can include a plurality of flaps separated by a plurality of slits.

In some embodiments, the method can further include extending the plurality of flaps through adjacent open cells of the frame and attaching the plurality of flaps to an outer skirt of the prosthetic valve.

In some embodiments, the method can further include folding each flap along a base of the flap so that the flap extends toward an inflow end of the prosthetic valve.

In some embodiments, the method can further include overlapping the plurality of flaps to adjacent pivot joints of the frame.

Some embodiments of the disclosure further concern another method of assembling a prosthetic valve. The method can include forming an annular frame by connecting a plurality of inner struts with a plurality of outer struts at a plurality of pivot joints. The plurality of inner struts can be configured to pivot relative to the plurality of outer struts at the plurality of pivot joints during radial expansion or compression of the frame. The method can also include attaching a plurality of leaflets to an inner skirt of the prosthetic valve. The leaflets can be configured to permit blood flow from an inflow end to an outflow end of the prosthetic valve and block blood flow from the outflow end to the inflow end of the prosthetic valve. The inner skirt can include a plurality of flaps separated by a plurality of slits. The method can further include extending the plurality of flaps through adjacent open cells of the frame and attaching the plurality of flaps to an outer skirt of the prosthetic valve.

In some embodiments, the method can further include folding each flap along a base of the flap so that the flap extends toward the inflow end of the prosthetic valve.

In some embodiments, the method can further include overlapping the plurality of flaps to adjacent pivot joints of the frame.

In some embodiments, the method can further include attaching one or more leaflet-support cords to the frame such that each cord extends along one of inner or outer struts at spaced apart locations and attaching the plurality of leaflets to the one or more leaflet-support cords.

In some embodiments, each of the one or more leaflet-supporting cords can include at least a first segment and a second segment. Attaching the one or more leaflet-supporting cords to the frame can include extending the first segment diagonally along one of the inner or outer struts and extending the second segment diagonally along another one of the inner or outer struts.

In some embodiments, the one or more leaflet-supporting cords can include a single continuous cord. Attaching the plurality of leaflets to the one or more leaflet-support cords can include attaching the plurality of leaflets to the single continuous cord.

In some embodiments, the one or more leaflet-supporting cords can include a plurality of leaflet-supporting cords. Attaching the plurality of leaflets to the one or more leaflet-support cords can include connecting each of the leaflet-supporting cords to a respective leaflet.

In some embodiments, each of the leaflet-supporting cords can include a plurality of anchoring portions and a plurality of suspended portions, and each suspended portion can extend between two adjacent anchoring portions. Attaching the one or more leaflet-supporting cords to the frame can include affixing the anchoring portions to respective anchoring features of the frame adjacent the pivot joints.

In some embodiments, affixing the anchoring portions to respective anchoring features of the frame can include extending the one or more leaflet-supporting cords through openings located in one or both of the inner and outer struts.

In some embodiments, affixing the anchoring portions to respective anchoring features of the frame can include extending the one or more leaflet-supporting cords through notches located in one or both of the inner and outer struts.

In some embodiments, affixing the anchoring portions to respective anchoring features of the frame can include affixing each of the anchoring portion to a pair of first and second anchoring features of the frame located at diametrically opposing locations of a respective pivot joint.

In some embodiments, affixing the anchoring portions to respective anchoring features of the frame can include forming one or more loops at a respective pivot joint by extending the corresponding leaflet-support cord through at least one anchoring feature and around a pair of inner and outer struts at the respective pivot joint.

In some embodiments, affixing the anchoring portions to respective anchoring features of the frame can include forming a self-locking knot at the one or more loops.

Certain embodiments of the disclosure concern a prosthetic valve assembly. The assembly can include a radially expandable and compressible annular frame. The frame can include a plurality of interconnected struts. The plurality of struts can include a plurality of inner struts and a plurality of outer struts. The inner struts can overlap adjacent outer struts at a plurality of pivot joints. Radial expansion or compression of the annular frame can cause the inner struts to pivot relative to the outer struts at the pivot joints. A channel can extend through at least one of the pivot joints. The assembly can also include an annular inner skirt covering at least a portion of an inner surface of the frame. The assembly can further include a valvular structure attached to the inner skirt and positioned within the frame. The valvular structure can be configured to permit the flow of blood from an inflow end to an outflow end of the valve and block the flow of blood from the outflow end to the inflow end of the valve. The inner skirt can be attached to the frame with a suture extending through the channel.

In some embodiments, the assembly can further include an annular outer skirt covering at least a portion of an outer surface of the frame. The suture can further extend through the outer skirt so as to attach the outer skirt to the frame.

In some embodiments, at least a portion of the outer skirt can extend into the channel so that the suture extending through the channel is at least partially surrounded by the portion of the outer skirt.

In some embodiments, the pivot joint having the channel can be formed by an inner strut overlapping with an outer strut. The inner or outer strut can include a projection and the other outer or inner strut can include an aperture. The projection can extend through the aperture.

In some embodiments, the projection can include a body portion and a flange portion. The flange portion can have a larger diameter than the body portion.

In some embodiments, the second strut can include a recess surrounding the aperture. The recess can be configured to receive the flange portion of the projection.

In some embodiments, the inner strut can include the projection and the outer strut can include the aperture.

In some embodiments, the outer strut can include the projection and the inner strut can include the aperture.

In some embodiments, the valvular structure can include a plurality of leaflets. Each leaflet can have an inflow edge portion. The inflow edge portions of the leaflets can define an undulating, curved scallop line.

In some embodiments, the inner skirt can include an outflow edge extending along a first row of strut segments that are located immediately adjacent to the scallop line toward the outflow end of the valve.

In some embodiments, the outflow edge of the inner skirt can be attached to the first row of strut segments via a continuous stitching pass that substantially tracks a curvature of the scallop line when the frame is in a radially expanded configuration.

In some embodiments, the inner skirt can include an inflow edge extending along a second row of strut segments that are located immediately adjacent to the scallop line toward the inflow end of the valve.

In some embodiments, the inflow edge of the inner skirt can be attached to the second row of strut segments via a continuous stitching pass that substantially tracks a curvature of the scallop line when the frame is in a radially expanded configuration.

Certain embodiments of the disclosure also concern a method of assembling a prosthetic valve. The method can include providing a plurality of inner struts, providing a plurality of outer struts, and forming an annular frame by connecting the inner and outer struts at a plurality of pivot joints. The inner struts can be configured to pivot relative to the outer struts at the plurality of pivot joints during radial expansion or compression of the frame. The method can also include attaching a valvular structure to an inner skirt. The valvular structure can be configured to permit the flow of blood from an inflow end to an outflow end of the valve and block the flow of blood from the outflow end to the inflow end of the valve. The method can further include attaching the inner skirt to the frame from an interior side of the frame.

In some embodiments, attaching the inner skirt to the frame can including passing a suture through the inner skirt and a channel extending through at least one of the pivot joints.

In some embodiments, the method can further include attaching an outer skirt to the frame from an exterior side of the frame by passing the suture through the outer skirt.

In some embodiments, the method can further include tensioning the suture so as to pull at least a portion of the outer skirt into the channel such that the suture passing through the channel is at least partially surrounded by the portion of the outer skirt.

In some embodiments, the channel can be formed by overlapping an inner strut with an outer strut. The inner or outer strut can include a projection and the other outer or inner strut can include an aperture. The projection can extend through the aperture.

In some embodiments, the valvular structure can include a plurality of leaflets. Each leaflet can have an inflow edge portion. The inflow edge portions of the leaflets can define an undulating, curved scallop line.

In some embodiments, the method can further include attaching an outflow edge of the inner skirt to a first row of strut segments that are located immediately adjacent to the scallop line toward an outflow end of the valve.

In some embodiments, the method can further include attaching an inflow edge of the inner skirt to a second row of strut segments that are located immediately adjacent to the scallop line toward an inflow end of the valve.

Certain embodiments of the disclosure further concern a prosthetic valve assembly including a radially expandable and compressible annular frame, an annular inner skirt covering at least a portion of an inner surface of the frame, and a valvular structure attached to the inner skirt and positioned within the frame. The frame can include a plurality of interconnected struts. The plurality of struts can include a plurality of inner struts and a plurality of outer struts. The inner struts can overlap adjacent outer struts at a plurality of pivot joints and radial expansion or compression of the annular frame causes the inner struts to pivot relative to the outer struts at the pivot joints. The valvular structure can be configured to permit the flow of blood from an inflow end to an outflow end of the valve assembly and block the flow of blood from the outflow end to the inflow end of the valve assembly. The valvular structure can include a plurality of leaflets. Each leaflet has an inflow edge portion, and the inflow edge portions of the leaflets can define an undulating, curved scallop line. The inner skirt can include an outflow edge extending along a first row of strut segments that are located immediately adjacent to the scallop line toward the outflow end of the valve assembly. The first row of strut segments can define a zig-zag shaped loop. The zig-zag shaped loop can include a plurality of first diagonal paths alternating with a plurality of second diagonal paths. Each of the first diagonal paths extends in a direction from the outflow end to the inflow end, and each of the second diagonal paths extends in a direction from the inflow end to the outflow end.

In some embodiments, the inner skirt can include an inflow edge extending along a second row of strut segments that are located immediately adjacent to the scallop line toward the inflow end.

In some embodiments, a portion of the scallop line traversing through a plurality of full cells of the frame can be bounded by the first and second rows of strut segments. Each of the full cells can have a quadrilateral shape formed by four interconnecting strut segments.

In some embodiments, the portion of the scallop line traversing through the plurality of full cells can intersect a plurality of crossing strut segments which extend between the first and second rows of strut segments. The inner skirt can be not attached to any of the crossing strut segments.

In some embodiments, at least two adjacent first and second diagonal paths can intersect at a lower pivot joint which is adjacent to an inflow-most location along the scallop line. The inflow-most location can be where the scallop line is closest to the inflow end.

In some embodiments, at least two adjacent first and second diagonal paths can intersect at an upper pivot joint which is adjacent to a commissure, and the commissure can be formed by a pair of adjacent leaflets and can be configured to be attached to the frame.

In some embodiments, an axial distance between the upper pivot joint and the commissure can be zero.

In some embodiments, the outflow edge of the inner skirt can be attached to the first row of strut segments.

In some embodiments, the inflow edge of the inner skirt can be attached to the second row of strut segments.

Certain embodiments of the disclosure further concern a method of assembling a prosthetic valve. The method can include forming an annular frame by connecting a plurality of inner struts and a plurality of outer struts at a plurality of pivot joints. The inner struts can be configured to pivot relative to the outer struts at the plurality of pivot joints during radial expansion or compression of the frame. The method can further include forming a sub-assembly by attaching a plurality of leaflets to an inner skirt and attaching the sub-assembly to the frame from an interior side of the frame.

In some embodiments, attaching the inner skirt to the frame can include passing a suture through the inner skirt and a channel extending through at least one of the pivot joints.

In some embodiments, the method can further include attaching an outer skirt to the frame from an exterior side of the frame by passing the suture through the outer skirt.

In some embodiments, the method can further include tensioning the suture so as to pull at least a portion of the outer skirt into the channel such that the suture passing through the channel is at least partially surrounded by the portion of the outer skirt.

In some embodiments, the channel can be formed by overlapping an inner strut with an outer strut. The inner or outer strut can include a projection and the other outer or inner strut can include an aperture, and the projection can extend through the aperture.

In some embodiments, the valvular structure can include a plurality of leaflets, each leaflet having an inflow edge portion. The inflow edge portions of the leaflets can define an undulating, curved scallop line.

In some embodiments, the method can further include attaching an outflow edge of the inner skirt to a first row of strut segments that are located immediately adjacent to the scallop line toward an outflow end of the valve.

In some embodiments, the method can further include attaching an inflow edge of the inner skirt to a second row of strut segments that are located immediately adjacent to the scallop line toward an inflow end of the valve.

The foregoing and other objects, features, and advantages of the invention will become more apparent from the following detailed description, which proceeds with reference to the accompanying figures.

BRIEF DESCRIPTION OF THE DRAWINGS

FIG. 5 is a flattened view of the inner skirt of the prosthetic valve depicted in FIGS. 3-4.

FIG. 6A is a perspective view of an embodiment of a flattened inner strut for a frame of a prosthetic valve, such as the frame of FIG. 3.

FIG. 6B is a perspective view of an embodiment of a flattened outer strut for a frame of a prosthetic valve, such as the frame of FIG. 3.

FIG. 6C is a perspective view of a hinge joint formed by the inner and outer struts depicted in FIGS. 6A-6B, according to one embodiment.

FIG. 9A is a perspective view of a pivot joint having an opening in one of the overlapping struts, according to one embodiment.

FIG. 9B is a perspective view of a pivot joint having two openings in one of the overlapping struts, according to one embodiment.

FIG. 9C is a perspective view of a pivot joint having two openings in one of the overlapping struts, according to another embodiment.

FIG. 14 is a cross-sectional view of a leaflet, an inner skirt attached to the leaflet and extending outside of a frame, and an outer skirt attached to the inner skirt, according to one embodiment.

FIG. 15 is a side elevation view of a portion of a frame depicting flaps of an inner skirt being attached to an outer skirt, according to one embodiment.

DETAILED DESCRIPTION

Described herein are examples of prosthetic implants, such as prosthetic heart valves that can be implanted within any of the native valves of the heart (e.g., the aortic, mitral, tricuspid and pulmonary valves). The present disclosure also provides frames for use with such prosthetic implants. The frames can comprise struts shaped to reduce or eliminate pinching of the soft components of the prosthetic implant (e.g., leaflets of the implant) when the implant is radially compressed to a delivery configuration for delivery into a patient.

Prosthetic valves disclosed herein can be radially compressible and expandable between a radially compressed state and a radially expanded state. Thus, the prosthetic valves can be crimped on or retained by an implant delivery apparatus in the radially compressed state during delivery, and then expanded to the radially expanded state once the prosthetic valve reaches the implantation site.

Figure 1:
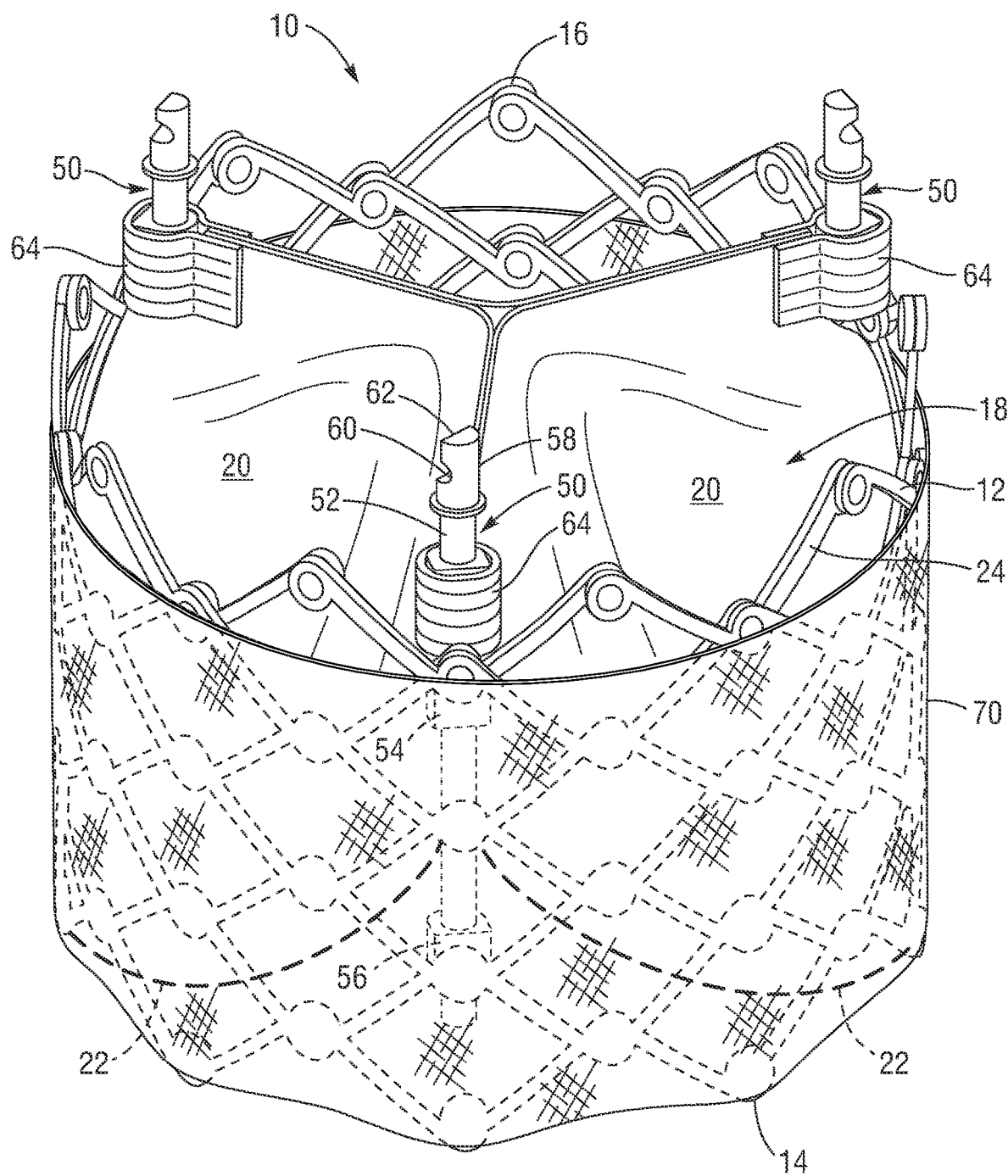
FIG. 1 is a side elevational view of a prosthetic valve, according to one embodiment.

FIG. 1 shows an exemplary prosthetic valve 10, according to one embodiment. The prosthetic valve 10 can include an annular stent or frame 12 having an inflow end 14 and an outflow end 16. The prosthetic valve 10 can also include a valvular structure 18 which is coupled to and supported inside of the frame 12. The valvular structure 18 is configured to regulate the flow of blood through the prosthetic valve 10 from the inflow end 14 to the outflow end 16.

The valvular structure 18 can include, for example, a leaflet assembly comprising one or more leaflets 20 made of a flexible material. The leaflets 20 can be made from in whole or part, biological material, bio-compatible synthetic materials, or other such materials. Suitable biological material can include, for example, bovine pericardium (or pericardium from other sources). The leaflets 20 can be secured to one another at their adjacent sides to form commissures, each of which can be secured to a respective actuator 50 or the frame 12.

In the depicted embodiment, the valvular structure 18 comprises three leaflets 20, which can be arranged to collapse in a tricuspid arrangement. Each leaflet 20 can have an inflow edge portion 22. As shown in FIG. 1, the inflow edge portions 22 of the leaflets 20 can define an undulating, curved scallop shape that follows or tracks a plurality of interconnected strut segments of the frame 12 in a circumferential direction when the frame 12 is in the radially expanded configuration. The inflow edges of the leaflets can be referred to as a "scallop line."

In some embodiments, the inflow edge portions 22 of the leaflets 20 can be sutured to adjacent struts of the frame generally along the scallop line. In other embodiments, the inflow edge portions 22 of the leaflets 20 can be sutured to an inner skirt (e.g., inner skirt 72 of FIGS. 3-5, discussed below), which in turn in sutured to adjacent struts of the frame. By forming the leaflets 20 with this scallop geometry, stresses on the leaflets 20 are reduced, which in turn improves durability of the valve 10. Moreover, by virtue of the scallop shape, folds and ripples at the belly of each leaflet 20 (the central region of each leaflet), which can cause early calcification in those areas, can be eliminated or at least minimized. The scallop geometry also reduces the amount of tissue material used to form valvular structure 18, thereby allowing a smaller, more even crimped profile at the inflow end 14 of the valve 10.

Further details regarding transcatheter prosthetic heart valves, including the manner in which the valvular structure can be mounted to the frame of the prosthetic valve can be found, for example, in U.S. Pat. Nos. 6,730,118, 7,393,360, 7,510,575, 7,993,394, and 8,252,202, and U.S. patent application Ser. No. 15/978,459 (Published as U.S. Publication No. 2018/0325665), all of which are incorporated herein by reference in their entireties.

Figure 2B:
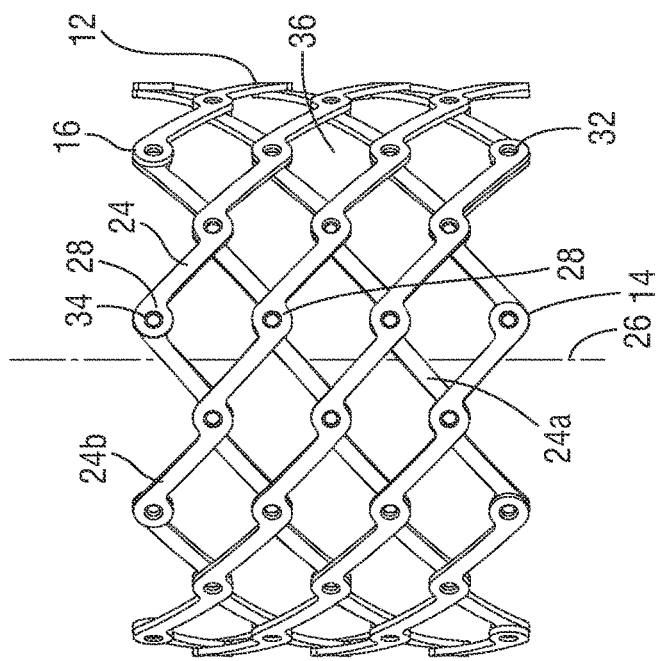
FIG. 2B shows the frame of the prosthetic valve of FIG. 1 shown in a radially expanded configuration.
Figure 2A:
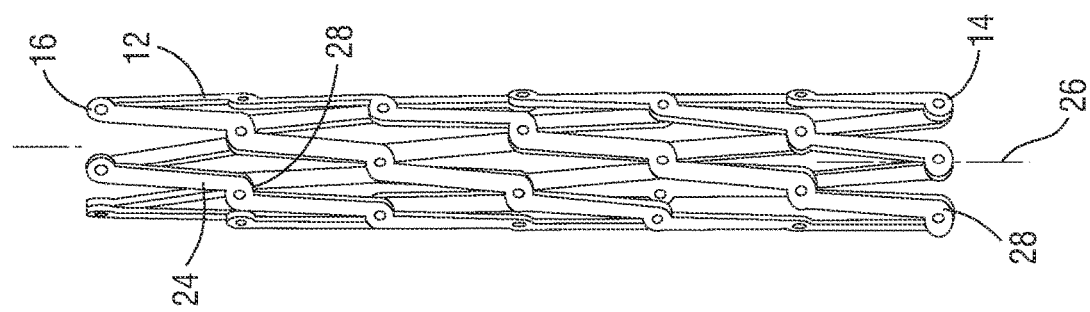
FIG. 2A shows the frame of the prosthetic valve of FIG. 1 in a radially compressed configuration.

The prosthetic valve 10 can be radially compressible and expandable between a radially compressed configuration and a radially expanded configuration. FIGS. 2A-2B show the bare frame 12 of the prosthetic valve 10 (without the leaflets and other components) for purposes of illustrating expansion of the prosthetic valve 10 from the radially compressed configuration (FIG. 2A) to the radially expanded configuration (FIG. 2B).

The frame 12 can include a plurality of interconnected lattice struts 24 arranged in a lattice-type pattern and forming a plurality of apices 34 at the outflow end 16 of the prosthetic valve 10. The struts 24 can also form similar apices 32 at the inflow end 14 of the prosthetic valve 10. In FIG. 2B, the struts 24 are shown as positioned diagonally, or offset at an angle relative to, and radially offset from, a longitudinal axis 26 of the prosthetic valve 10 when the prosthetic valve 10 is in the expanded configuration. In other implementations, the struts 24 can be offset by a different amount than depicted in FIG. 2B, or some or all of the struts 24 can be positioned parallel to the longitudinal axis 26 of the prosthetic valve 10.

The struts 24 can comprise a set of inner struts 24a (extending from the upper left to the lower right of the frame in FIG. 2B) and a set of outer struts 24b (extending from the lower left to the upper right of the frame in FIG. 2B) connected to the inner struts 24a. The open lattice structure of the frame 12 can define a plurality of open frame cells 36 between the struts 24.

The struts 24 can be pivotably coupled to one another at one or more pivot joints 28 along the length of each strut. For example, in one embodiment, each of the struts 24 can be formed with apertures at opposing ends of the strut and apertures spaced along the length of the strut. Respective hinges can be formed at the locations where struts 24 overlap each other via fasteners, such as rivets or pins that extend through the apertures. The hinges can allow the struts 24 to pivot relative to one another as the frame 12 is radially expanded or compressed, such as during assembly, preparation, or implantation of the prosthetic valve 10.

The frame struts and the components used to formed the pivot joints of the frame 12 (or any frames described below) can be made of any of various suitable materials, such as stainless steel, a cobalt chromium alloy, or a nickel titanium alloy ("NiTi"), for example Nitinol. In some embodiments, the frame 12 can be constructed by forming individual components (e.g., the struts and fasteners of the frame) and then mechanically assembling and connecting the individual components together. In other embodiments, the struts 24 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic valve are described in U.S. Patent Publication Nos. 2018/0153689 and 2018/0344456, and U.S. patent application Ser. Nos. 16/105, 353 and 62/748,284, all of which are incorporated herein by reference.

In the illustrated embodiment, the prosthetic valve 10 can be mechanically expanded from the radially configuration to the radially expanded configuration. For example, the prosthetic valve 10 can be radially expanded by maintaining the inflow end 14 of the frame 12 at a fixed position while applying a force in the axial direction against the outflow end 16 toward the inflow end 14. Alternatively, the prosthetic valve 10 can be expanded by applying an axial force against the inflow end 14 while maintaining the outflow end 16 at a fixed position, or by applying opposing axial forces to the inflow and outflow ends 14, 16, respectively.

As shown in FIG. 1, the prosthetic valve 10 can include one or more actuators 50 mounted to and equally spaced around the inner surface of the frame 12. Each of the actuators 50 can be configured to form a releasable connection with one or more respective actuators of a delivery apparatus.

In the illustrated embodiment, expansion and compression forces can be applied to the frame by the actuators 50. Referring again to FIG. 1, each of the actuators 50 can comprise a screw or threaded rod 52, a first anchor in the form of a cylinder or sleeve 54, and a second anchor in the form of a threaded nut 56. The rod 52 extends through the sleeve 54 and the nut 56. The sleeve 54 can be secured to the frame 12, such as with a fastener that forms a hinge at the junction between two struts. Each actuator 50 is configured to increase the distance between the attachment locations of a respective sleeve 54 and nut 56, which causes the frame 12 to elongate axially and compress radially, and to decrease the distance between the attachment locations of a respective sleeve 54 and nut 56, which causes the frame 12 to foreshorten axially and expand radially.

For example, each rod 52 can have external threads that engage internal threads of the nut 56 such that rotation of the rod causes corresponding axial movement of the nut 56 toward or away from the sleeve 54 (depending on the direction of rotation of the rod 52). This causes the hinges supporting the sleeve 54 and the nut 56 to move closer towards each other to radially expand the frame or to move farther away from each other to radially compress the frame, depending on the direction of rotation of the rod 52.

In other embodiments, the actuators 50 can be reciprocating type actuators configured to apply axial directed forces to the frame to produce radial expansion and compression of the frame. For example, the rod 52 of each actuator can be fixed axially relative to the sleeve 56 and slidable relative to the sleeve 54. Thus, in this manner, moving the rod 52 distally relative to the sleeve 54 and/or moving the sleeve 54 proximally relative to the rod 52 radially compresses the frame. Conversely, moving the rod 52 proximally relative to the sleeve 54 and/or moving the sleeve 54 distally relative to the rod 52 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a subcomponent of the actuators themselves.

Each rod 52 can include an attachment member 58 along a proximal end portion of the rod 52 configured to form a releasable connection with a corresponding actuator of a delivery apparatus. The actuator(s) of the delivery apparatus can apply forces to the rods for radially compressing or expanding the prosthetic valve 10. The attachment member 58 in the illustrated configuration comprises a notch 60 and a projection 62 that can engage a corresponding projection of an actuator of the delivery apparatus.

In the illustrated embodiments, the prosthetic valve 10 includes three such actuators 50, although a greater or fewer number of actuators could be used in other embodiments. The leaflets 20 can have commissure attachments members 64 that wrap around the sleeves 54 of the actuators 50. Further details of the actuators, locking mechanisms and delivery apparatuses for actuating the actuators can be found in U.S. Patent Publication No. 2018/0153689 and U.S. patent application Ser. Nos. 16/105,353, 15/831,197, and 15/978,459, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

The prosthetic valve 10 can include one or more skirts or sealing members. As described more fully below, the prosthetic valve 10 can include an inner skirt (e.g., inner skirt 72 of FIGS. 3-5, discussed below) mounted on the inner surface of the frame. The inner skirt can function as a sealing member to prevent or decrease perivalvular leakage, to anchor the leaflets to the frame, and/or to protect the leaflets against damage caused by contact with the frame during crimping and during working cycles of the prosthetic valve. As shown in FIG. 1, the prosthetic valve 10 can also include an outer skirt 70 mounted on the outer surface of the frame 12. The outer skirt 70 can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials, including fabrics (e.g., polyethylene terephthalate fabric) or natural tissue (e.g., pericardial tissue).

Figure 3:
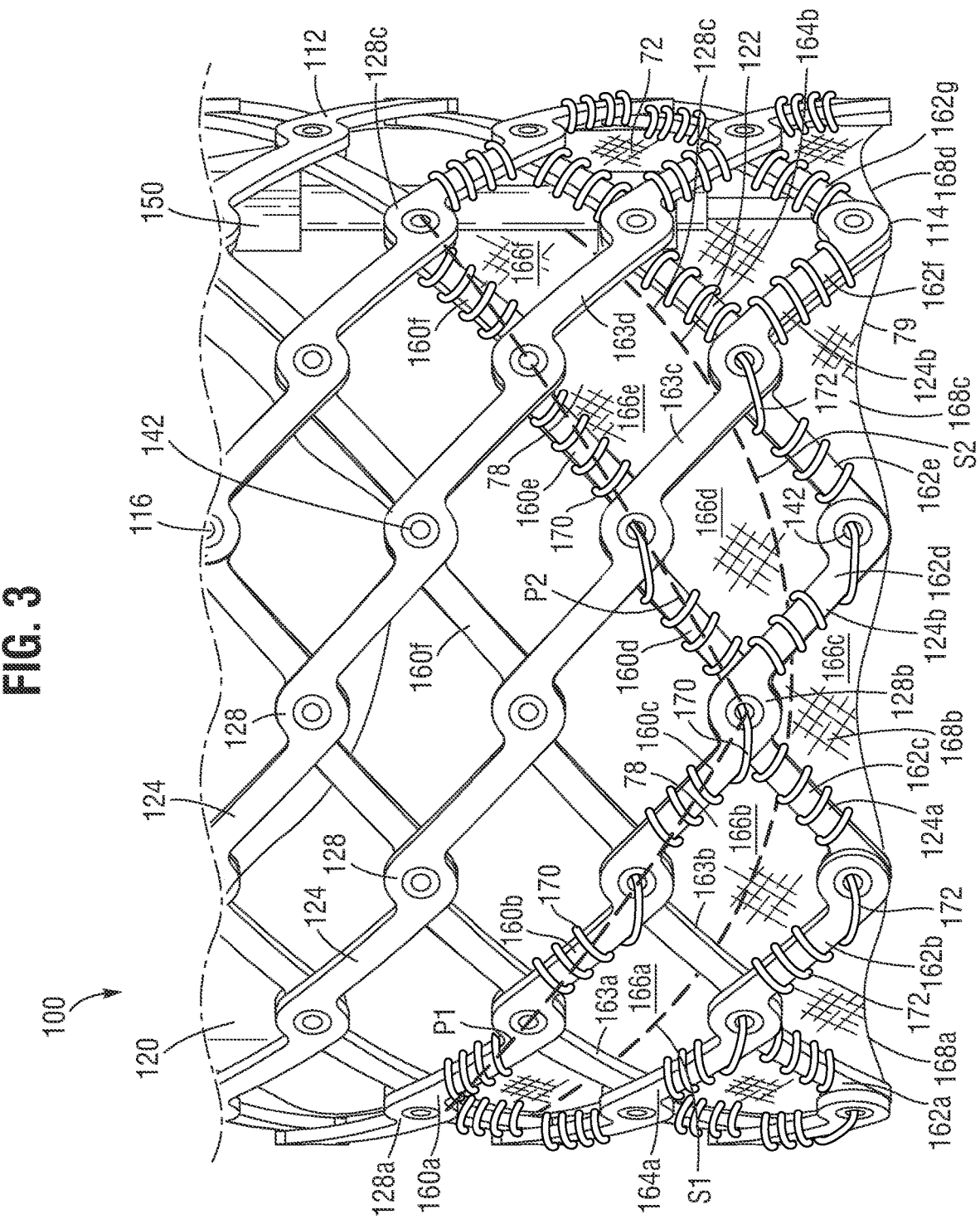
FIG. 3 shows a side elevational view a prosthetic valve, according to another embodiment.
Figure 4:
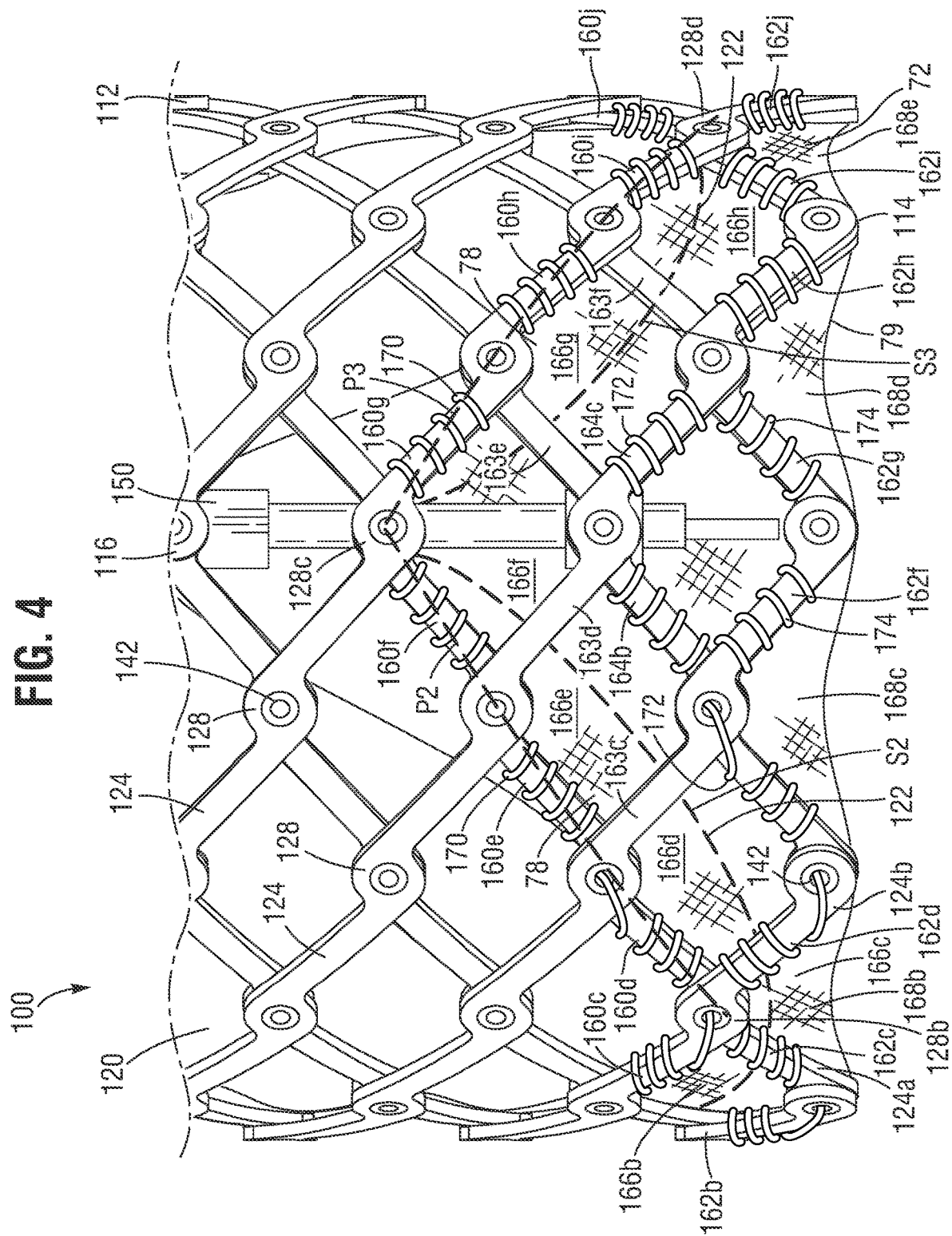
FIG. 4 is another side elevational view of the embodiment depicted in FIG. 3.

FIGS. 3-4 shows another embodiment of a prosthetic valve 100. Similar to the prosthetic valve 10 depicted in FIG. 1, the prosthetic valve 100 includes a frame 112 which can be radially compressed and expanded by one or more actuators 150 (similar to actuators 50) mounted on the interior surface of the frame 112. Likewise, the prosthetic valve 100 includes a plurality of leaflets 120 which are configured to regulate the flow of blood through the prosthetic valve 100 from the inflow end 114 to the outflow end 116 of the frame 112. The description above of the leaflets 20, including the shape of the leaflets 20, applies to the leaflets 120. As such, the inflow edge of the leaflets 120 can form a scallop line 122.

Similar to the frame 12 depicted in FIG. 1, the frame 112 includes a plurality of interconnected lattice struts 124 arranged in a lattice-type pattern, and the struts 124 can be pivotably coupled to one another at one or more pivot joints 128 along the length of each strut. As described more fully below, one or more of the pivot joints 128 can have a channel which extends through the corresponding pivot joint 128.

As shown in FIGS. 3-4, the prosthetic valve 100 includes an inner skirt 72 attached to the inner surface of the frame 112. FIG. 5 shows a flattened view of the inner skirt 72. Optionally, an outer skirt (similar to the outer skirt 70 depicted in FIG. 1) can also be attached to the outer surface of the frame 112 (not shown). As described in greater detail below, in the illustrated embodiment, the leaflets are sutured to the inner skirt 72 along the scallop line 122, such as with in-and-out stiches that extend through the leaflets and the inner skirt. Thus, in the embodiment of FIGS. 3-4, the scallop line 122 also represents the stitching that is used to secure the inflow edges of the leaflets 120 to the inner skirt 72.

In some embodiments, the size of the inner skirt 72 can be minimized to improve the process for assembling the prosthetic valve 100 and to reduce the risk of abrasion to the leaflets 120, which can be caused by the edges of the inner skirt and sutures attached on the struts, especially during systole.

In one embodiment, as illustrated in FIGS. 3-4, minimization of the inner skirt 72 can be achieved by sizing and shaping the inner skirt 72 so that when it is attached to the inflow end portion of the frame 112, the scallop line 122 formed by the inflow edges of the leaflets 120 is fully covered by the inner skirt 72 while the outflow edge of the inner skirt (the upper edge in the figures) extends only to the struts that are immediately adjacent to the scallop line 122 toward the outflow end 116 of the frame 112.

For example, FIGS. 3-4 show that the scallop line 122 passes through the full cells 166a-b and 166d-h near the inflow end portion of the frame 112 for an about 180-degree segment of the scallop line (note that the other about 180-degree segment of the scallop line can pass through additional full cells, which are not shown in FIGS. 3-4). The scallop line 122 also passes through some areas adjacent to the inflow end 114 of the frame that do not have full frame cells (e.g., area 166c depicted in FIGS. 3-4, which is a half-cell below two overlapping struts 124a, 124b that extend to the inflow end 114 of the frame). As used herein, a full cell means a frame cell with a quadrilateral shape formed by four interconnecting strut segments, and half-cell means a frame cell that has only two sides formed by two connected strut segments.

As shown, the outflow edge 78 of the inner skirt 72 can run along a first row of strut segments comprising 160a-j that are located immediately adjacent to the scallop line 122 toward the outflow end 116 of the frame. Although the labelled strut segments 160a-j form approximately a 180-degree segment, it should be understood that the entire first row of strut segments for supporting the outflow edge 78 of the inner skirt would extend 360 degrees.

The outflow edge 78 of the inner skirt 72 can be attached to the first row of strut segments, for example, with one or more sutures forming whip stitches 170. In some embodiments, the stiches 170 can form a continuous stitching pass that substantially tracks or parallels the scallop line 122 when the frame 112 is in a radially expanded configuration. The whip stitches 170 can extend around the strut segments, through the skirt 78, and optionally through openings or channels 142 at the pivot joints between two overlapping struts, as shown in FIGS. 3 and 4. Such a continuous stitching pass can reduce stitch amount and improve stitch simplicity and continuity in the valve assembly process.

By lowering and attaching the outflow edge 78 of the inner skirt 72 along the first row of strut segments that are located immediately adjacent to the scallop line 122 toward the outflow end 116 of the frame, the risk of leaflet abrasion can be mitigated because the outflow edge 78 and the associated stitches 170 are closer to the leaflet bending line and farther away from the area where the leaflets 120 may hit the inner wall of the frame.

As noted above, the first row of strut segments supporting the outflow edge 78 of the inner skirt generally tracks the curvature of the scallop line 122. For example, as shown in FIG. 3, the strut segments 160a, 160b and 160c form a diagonal path P1 extending from a pivot joint 128a adjacent one of the commissures, to a pivot joint 128b adjacent the inflow-most edge portion of the leaflet closest to the inflow end of the frame (the inflow-most edge portion is half-way between the commissures tabs of the leaflet in the depicted embodiment). The diagonal path P1 extends along a diagonal line in a direction from the outflow end of the frame to the inflow end of the frame and therefore generally tracks the curvature of the adjacent scallop line segment S1, which also extends in a direction from the outflow end of the frame to the inflow end of the frame starting at the upper end of the segment S1 adjacent the commissure to the lower end of the segment S1 at the inflow-most edge portion of the leaflet.

Similarly, as shown in FIGS. 3-4, the strut segments 160d, 160e and 160f form a diagonal path P2 extending from the pivot joint 128b to a pivot joint 128c adjacent the opposite commissure of the leaflet, and the strut segments 160g, 160h and 160i form a diagonal path P3 extending from the pivot joint 128c to a pivot joint 128d at the inflow-most edge portion of the adjacent leaflet. The diagonal path P2 extends along a diagonal line in a direction from the inflow end of the frame to the outflow end of the frame and therefore generally tracks the curvature of the adjacent scallop line segment S2, which also extends in a direction from the inflow end of the frame to the outflow end of the frame starting at the lower end of the segment S2 to the upper end of the segment S2 adjacent the opposite commissure of the leaflet. The diagonal path P3 extends along a diagonal line similar to P1 but tracks the adjacent scallop line segment S3 of the next leaflet.

As such, the paths P1 and P2 intersect at the pivot joint 128b which is adjacent the inflow-most location along the scallop line 122 which is closest to the inflow end (i.e., the joint between segments S1 and S2), and the paths P2 and P3 intersect at the pivot joint 128c which is adjacent to the point at the scallop line 122 which is closest to the outflow end (i.e., the joint between segments S2 and S3).

As can be appreciated, at each leaflet 120, the outflow edge 78 of the skirt 72 is attached to strut segments along a first diagonal path (e.g., P1) extending in a direction from the outflow end to the inflow end of the frame and then along a second path (e.g., P2) extending in the opposite direction from the inflow end to the outflow end of the frame.

For the entire first row of strut segments for supporting the outflow edge 78, such diagonal paths form a zig-zag path or row of strut segments that extends 360 degrees around the frame, forming a closed zig-zap loop of strut segments. When attaching the inner skirt 72 as shown in FIG. 5 to the frame 112, the closed zig-zag loop of strut segments can include three paths (one for each leaflet 120) (e.g., P1 and P3) extending in a direction from the outflow end to the inflow end of the frame alternating with three paths (one for each leaflet 120) (e.g., P2) extending in a direction from the inflow end to the outflow end of the frame. In the illustrated embodiment (which includes three leaflets 120), the intersections of these paths include three pivot joints (e.g., 128c) that are adjacent the commissures and three pivot joints (e.g., 128b) that are adjacent the inflow-most location of each leaflet 120.

As noted above, adjacent leaflets can form commissures which can be secured to respective actuators. For example, two adjacent leaflets corresponding to the scallop line segments S2 and S3 can form a commissure (not shown) which is secured to the actuator 150 at the outflow end of the frame. As best shown in FIG. 4, the upper ends of the scallop line segments S2 and S3 meet at a location adjacent a pivot joint 128c along the row of strut segments. In some embodiments, the axial distance (or gap) between the commissure and the pivot joint 128c can be reduced or even eliminated. Reducing such axial distance can reduce stress concentrations on the scallop line stiches during valve expansion and valve cycling and provide a more robust connection of the leaflets to the skirt.

In the embodiment depicted in FIGS. 3-4, the inflow edge 79 of the inner skirt 72 can extend to and generally align with the inflow end 114 of the frame. In the flattened configuration (FIG. 5), the inflow edge 79 of the inner skirt 72 is straight in the illustrated embodiment. As such, the inflow edge 79 of the inner skirt 72 and the inflow-end strut segments (162a-j) that define the inflow end 114 can form a plurality of triangular areas 168a-e along the inflow edge portion of the inner skirt.

In the illustrated embodiment, the inflow edge 79 (or a portion adjacent to the inflow edge 79) of the inner skirt 72 can be attached to a second row of strut segments comprising 164a, 162b-e, 164b-c, 162h-j that are located immediately adjacent to the scallop line 122 toward the inflow end 114 of the frame. Strut segments 164a, 162b-e, 164b-c, 162h-j form an about 180-degree segment of the second row. The entire second row of strut segments for supporting the inflow edge 79 of the inner skirt would extend 360 degrees around the frame. Thus, the entire second row comprises two partial rows formed from strut segments 164a, 162b-e, 164b-c, 162h-j. The inflow edge 79 can be attached to the second row of strut segments with one or more sutures forming whip stitches 172 that can extend around adjacent strut segments, through the inner skirt, and optionally through the openings or channels 142 at the pivot joints between overlapping struts. In some embodiments, the stiches 172 can form a continuous stitching pass that substantially tracks or parallels the scallop line 122 when the frame 112 is in a radially expanded configuration. Such a continuous stitching pass can reduce stitch amount and improve stitch simplicity and continuity in the valve assembly process.

As shown in FIGS. 3-4, the first and second rows of strut segments respectively supporting the outflow edge 78 and inflow edge 79 generally form two guard rails that bound the scallop line 122 except for the portions of the scallop line that are closest to the inflow end of the frame, where the scallop line 122 may intersect some second row strut segments (e.g., 162c, 162d) that form half-cells (e.g., 166c). For any other full cells (e.g., 166a-b, 166d-h) through which the scallop line 122 traverses, the scallop line 122 is bounded between the first and second rows of strut segments.

In some embodiments, besides stitching the inner skirt 72 along the two rows of strut segments which bound the scallop line 122, additional stitches 174 can be applied to suture selected portions of the inner skirt 72 to selected strut segments (e.g., 162f, 162g) to reduce or minimize areas of inner skirt that otherwise would be loose or detached from the frame.

As shown in FIGS. 3-4, the scallop line 122 intersects a plurality of strut segments (e.g., 163a-d, hereinafter "crossing strut segments") which extend between the first and second rows and form a side that is shared by two adjacent full cells (e.g., 166a-b, 166d-h). In some embodiments, the inner skirt 72 is not stitched to such crossing strut segments (163a-d). The stitch-free crossing strut segments (163a-d) allow the adjacent portions of the inner skirt 72 to be pulled inwardly to create a tenting effect when the leaflets move inwardly toward the closed position of the leaflets during valve cycling so as to reduce stress on the leaflets.

In other embodiments, the inflow edge 79 of the inner skirt 72 can be shaped to correspond with the path formed by the second row of strut segments comprising 164a, 162b-e, 164b-c, 162h-j. As such, frame cells that are completely covered by the inner skirt 72 are limited to those frame cells through which the scallop line 122 traverses (e.g., 166a-b, 166d-h).

In some embodiments, the leaflets 120 can be attached to the inner skirt 72 to form a sub-assembly before attaching the inner skirt 72 to the frame 112. In other words, some soft components (e.g., leaflets and inner skirt) can be pre-assembled. In one particular embodiment, the leaflets 120 can be sutured to the inner skirt 72 along the scallop line 122, and the leaflet and skirt sub-assembly can then be placed inside of the frame 112, and then the inner skirt 72 can be sutured to the strut segments of the frame as described above and the commissures can be attached to the frame as previously described. Thus, the process of assembling the prosthetic valve can be more efficient and the risk of damaging the leaflets can be reduced due to less stitching operations close to the leaflets.

In some embodiments, one or more pivot joints 128 of the frame 112 can have a channel that allows a suture to extend through, as described more fully below.

FIG. 6A shows an exemplary inner strut 124a and FIG. 6B shows an exemplary outer strut 124b. FIG. 3C shows one particular embodiment of a pivot joint 128 formed by the pair of overlapping inner strut 124a and outer strut 124b. A frame 112 (similar to frame 12) can be formed from a plurality of inner struts 124a and outer struts 124b arranged in the same manner as struts 24 discussed above.

As shown in FIG. 6A, the inner strut 124a can have an offset, or zig-zag, pattern defined by a plurality of offset linear portions or segments 126a. The linear segments 126a in the illustrated embodiment are arranged end-to-end relative to each other with adjacent ends interconnected to each other by intermediate segments 130a. The inner strut 124a can have enlarged end portions 132a that form the apices at the inflow and outflow end of the frame.

In the embodiment shown in FIG. 6A, each of the intermediate segments 130a and end portions 132a has a respective projection 134a at its geometric center. In some other embodiments (not shown), only some, not all, of the intermediate segments 130a and end portions 132a have the projections 134a.

As shown in FIG. 6A, the projection 134a can include a body portion 136a and a flange portion 138a, and the flange portion 138a can have a larger radial cross-sectional dimension (e.g., diameter) than the body portion 136a. In the depicted embodiment, the flange portion 138a is located at the distal end of the body portion 136a. In other embodiments, the flange portion 138a can be located at the middle portion of the body portion 136a.

In some embodiments, the body portion 136a has a generally cylindrical shape. In other embodiments, the body portion 136a can have a non-cylindrical shape. For example, the cross-section of the body portion 136a can have the shape of an oval, a rectangle, a square, or others. In another example, the cross-sectional area of the body portion 136a can vary along the axial length of the projection 134a. In some embodiments, the cross-section of the flange portion 138a can have a generally circular shape. In other embodiments, the cross-section of the flange portion 138a can have a non-circular shape, such as a rectangle, a hexagon, or others.

As shown, the projection 134a has a passage 140a extending through the body portion 136a and the flange portion 138a. As described more fully below, the passage 140a can define a channel through which a suture can pass through for securing the soft components of the prosthetic valve (e.g., the leaflets and/or the inner skirt) to the frame.

Still referring to FIG. 6A, each linear segment 126a can be slightly laterally offset from an adjacent linear segment 126a in a direction perpendicular to the overall length of the strut 124a to provide the zig-zag pattern to the inner strut. The amount of offset of each linear segment 126a relative to an adjacent linear segment 126a along the length of the inner strut 124a can be constant such that an imaginary line 125a can pass through the geometric center of each intermediate segment 130a along the entire length of the inner strut 124a. In alternative embodiments, the amount of offset between two adjacent linear segments 126a can vary along the length of the inner strut 124a. For example, the amount of offset between linear segments 126a adjacent the outflow end of the frame can be greater than the amount of offset between linear segments 126a adjacent the inflow end of the frame, or vice versa.

The linear segments 126a can include at least substantially flat or linear opposing longitudinal edges 144a, 146a extending between curved or rounded edges 148a of the intermediate segments 130a. In alternative embodiments, the opposing edges 148a of the intermediate segments 130a can be substantially flat or linear edges that extend at an angle between respective ends of the edges 144a, 146a of the liner segments 126a.

As shown in FIG. 6A, the width W1 of each liner segment 126a is defined as the distance measured between the opposing edges 144a, 146a of a segment 126a. In the illustrated embodiment, the width W1 is constant along the length of the inner strut 124a. As such, each longitudinal edge 144a is laterally offset from an adjacent longitudinal edge 144a of an adjacent linear segment 126a, and each longitudinal edge 146a is laterally offset from an adjacent longitudinal edge 146a of an adjacent linear segment 126a. The width W2 of each intermediate segment 132a and end portion 134a can be greater than the width W1 of the linear segments 126a.

In alternative embodiments, the width W1 of each linear segment 126a can vary along the length of a strut. For example, the width W1 of a linear segment 126a adjacent the inflow end of the frame can be greater than the width W1 of a linear segment 126a adjacent the outflow end of the frame, or vice versa. Further, where the width W1 of the linear segments 126a vary along the length of an inner strut 124a, a linear segment 126a can have one longitudinal edge 144a or 146a that is collinear with a longitudinal edge of an adjacent linear segment on the same side of the inner strut, while the other longitudinal edge 144a, 146a is laterally offset from the longitudinal edge of an adjacent linear segment on the same side of the inner strut. In other words, the inner strut 124a can have an overall zigzag or offset pattern by virtue of the varying widths W1 of the linear segments.

Referring to FIG. 6B, the outer strut 124b can also have an offset, or zigzag, pattern defined by a plurality of offset linear portions or segments 126b. The linear segments 126b in the illustrated embodiment are arranged end-to-end relative to each other with adjacent ends interconnected to each other by intermediate segments 130b, and the outer strut 124b can have enlarged end portions 132b that form the apices at the inflow and outflow end of the frame.

The outer strut 124b can be configured to have generally the same shape and size as the inner struts 124a except in the intermediate segments 130b and end portions 132b. As shown in FIG. 6B, each of the intermediate segments 130b and end portions 132b has a respective aperture 134b at its geometric center. In some other embodiments (not shown), only some, not all, of the intermediate segments 130b and end portions 132b have the apertures 134b. In the depicted embodiment, the aperture 134b has a generally circular shape. In other embodiments, the aperture 134b can have non-circular shapes such as oval, rectangle, square, or others.

Each of the projections 134a on the inner strut 124a can be configured to extend through a corresponding aperture 134b in the outer strut 124b. For example, each of the apertures 134b can be sized and shaped so that when an intermediate segment 130b (or end portion 132b) of the outer strut 124b overlaps with an intermediate segment 130a (or end portion 132a) of the inner strut 124a, the body portion 136a of the projection 134a at the intermediate segment 130a (or end portion 132a) of the inner strut 124a can extend through the corresponding aperture 134b at the intermediate segment 130b (or end portion 132b) of the outer strut 124b.

The cross-sectional dimension of the flange portion 138a of the projection 134a (e.g., diameter) can be larger than that of the corresponding aperture 134b so as to prevent the inner strut 124a from disconnecting from the outer strut 124b after the projection 134a is inserted through the aperture 134b.

The flange portion 138a can be formed in many different ways. For example, in one embodiment, the projection 134a can be initially configured to have only a body portion 136a made of a plastically deformable material. After inserting the body portion 136a through the aperture 134b, the flange portion 138a can be created by deforming (e.g., by impacting or pressing) the distal end portion of the body portion 136a. In another embodiment, the flange portion 138a can be coupled to the body portion 136a (e.g., by gluing, thermal binding, welding or other means) after the body portion 136a is inserted through the aperture 134b. In yet another embodiment, the projection 134a can comprise an elastic or shape memory material such that the flange portion 138a can be elastically deformed to have a reduced cross-sectional dimension for inserting through the aperture 134b and then return to non-deformed, original shape extending radially outwardly from the body portion 136a.

Still referring to FIG. 6B, each of the intermediate segments 130b and end portions 132b of the outer strut 124b can include a recess 136b surrounding the aperture 134b. In the depicted embodiment, each recess 136b is configured to receive the flange portion 138a of a corresponding projection 134a.

In the depicted embodiment, each recess 136b is configured as a counterbore with a flat bottom surface surrounding the aperture 134b. In other embodiments, the recess 136b can be configured as a countersink with a conical sidewall that extends to the aperture 134b.

As illustrated in FIG. 6C, a pivot joint 128 can be formed by overlapping the inner strut 124a with the outer strut 124b and extending one projection 134a through a corresponding aperture 134b. The axial length of the aperture 134b can be approximately the same as the axial length of the body portion 136a. In addition, the size and shape of the recess 136b can be approximately the same as those of the flange portion 138a. Thus, in the fully formed joint 128, the body portion 136a of the projection 134a is disposed in the aperture 134b, the flange portion 138a can be snuggly received in the recess 136b and desirably does not extend beyond the outer surface of the outer strut 124b. In the illustrated embodiment, the outer surface of the flange portion 138a is co-planar with the outer surface of the outer strut 124b.

Although FIGS. 6A-6C show the pivot joint 128 formed by the projection 134a on the inner strut 124a extending through the aperture 134b on the outer strut 124b, it should be understood that the pivot joint 128 can be formed in a reversed configuration. For example, the pivot joint 128 can be formed by a projection located on the outer strut extending through an aperture located on the inner strut.

Figure 7:
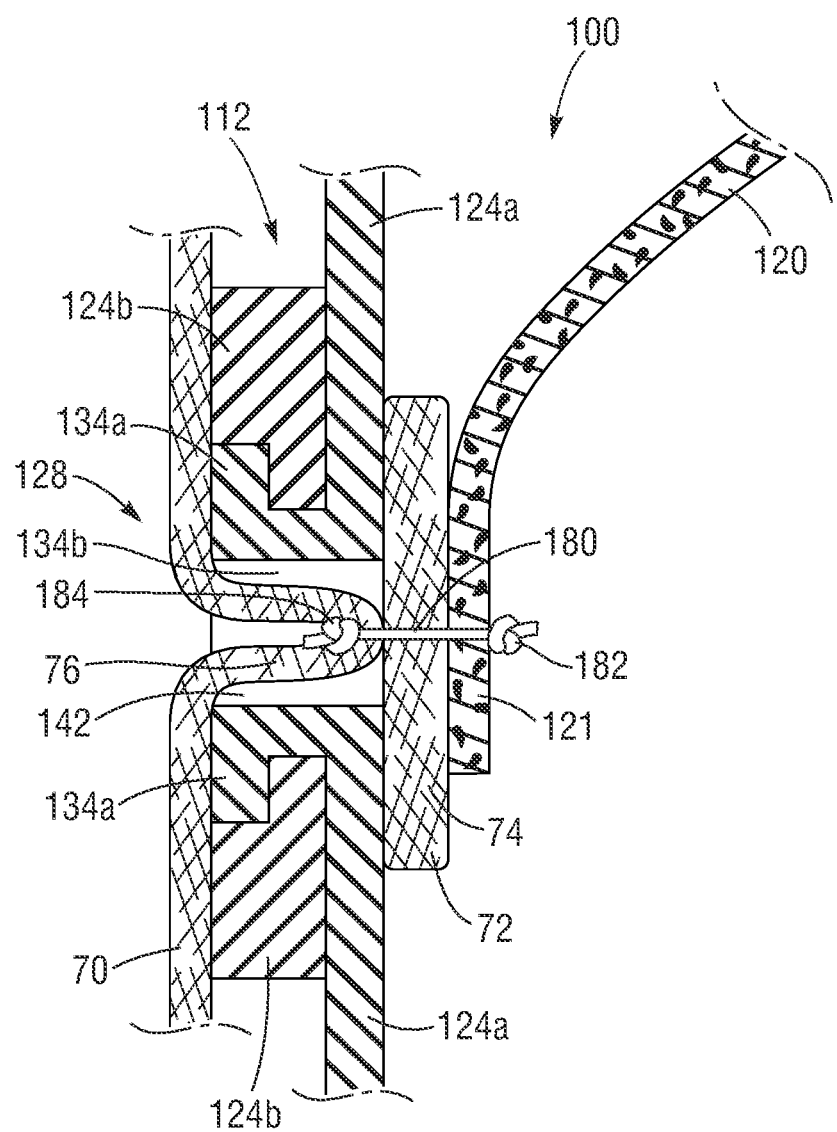
FIG. 7 is a side cross-sectional view of a hinge joint of a prosthetic valve including the adjacent portions of inner and outer skirts, according to one embodiment.

FIG. 7 shows a side cross-sectional view of one pivot joint 128 of a prosthetic valve that is formed by a pair of an overlapping inner strut 124a and outer strut 124b. FIG. 7 also illustrates a method of attaching an inner skirt 72 and a plurality of leaflets 120 to the frame 112, according to one embodiment. Although only one leaflet is shown in FIG. 7, it should be understood that the prosthetic valve can have a plurality of leaflets, such as three leaflets arranged in a tricuspid configuration in the same manner as the leaflets 20 in FIG. 1. In this embodiment, the outflow edge 78 of the inner skirt 72 can have an undulating shape that corresponds to the curvature of the inflow edges of the leaflets 120.

As shown, the projection 134a on the inner strut 124a extends through the aperture 134b on the outer strut 124b, and the passage 140a in the projection 134a forms a channel 142 extending through the pivot joint 128. An inflow edge portion 121 of a leaflet 120 can be attached to the inner skirt 72. The inner skirt 72 is configured to cover at least a portion of the inner surface of the frame 112. The attachment of the leaflet 120 to the inner skirt 72 can be achieved by a variety of means, such as stitching, gluing, etc.

For example, the inner skirt 72 can be attached to the frame 112 by a suture 180, which can extend through the channel 142 in the pivot joint 128. In the depicted embodiment, the suture 180 extends from the interior side of the frame 112, passes though the leaflet 120 and the inner skirt 72, and then further extends through the channel 142. Thus, in this embodiment, unlike FIGS. 3-4, the scallop line formed by the inflow edges of the leaflets are attached to a zig-zag row of strut segments extending around the frame.

In the depicted embodiment, the suture 180 extending through the channel 142 further passes through an outer skirt 70 such that the inner skirt 72 and the outer skirt 70 are attached to each other. The outer skirt 70 is configured to cover at least a portion of an outer surface of the frame 112.

As shown, the suture 180 can be configured to form an inner knot 182 located inside of the frame (e.g., located at an inner surface of the leaflet if the suture 180 extends through the leaflet) and an outer knot 184 located at the outer surface of the outer skirt 70 so as to tighten the inner skirt 72 and outer skirt 70 around the interior and exterior sides the pivot joint 128.

As shown, at least a portion 76 of the outer skirt 70 can extend into the channel 142 so that the suture 180 extending through the channel 142 is completely surrounded by the portion 76 of the outer skirt 70. This can be achieved, for example, by tensioning or tightening the suture 180 so as to pull at least the portion 76 of the outer skirt 70 into the channel 142. In this manner, the portion 76 of the outer skirt 70 can protect the suture 180 from friction with the surrounding rivet area.

In some embodiments, the portion 76 of the outer skirt 70 is only partially pulled into the channel 142 such that the suture 180 extending through the channel 142 is only partially surrounded by the portion 76 of the outer skirt 70.

In some embodiments (not shown), the suture 180 can pass through the inner skirt 72 and extend through the channel 142 without passing through the leaflet 120 (similar to the embodiment of FIGS. 3-4) (in which case the knot 182 can be located between the inner skirt 72 and the leaflet 120 and the leaflet 120 can be connected to the inner skirt 72 or to struts of the frame using separate sutures or other connection means).

In some embodiments, the suture 180 extending through the channel 142 can be wrapped around the adjacent inner strut 124a or outer strut 124b instead of being tied off or knotted at a single pivot joint 128.

For example, in some embodiments, the suture 180 can extend through the channel 142, the inner skirt 72, the outer skirt 70, and optionally a leaflet 120 at one pivot joint 128, wrap around a strut 124a, 124b one or more times in a whip stitch configuration (similar to the embodiment of FIGS. 3-4), and then extend through the channel 142 of an adjacent pivot joint 128, the inner skirt, the outer skirt, and optionally a leaflet at the adjacent pivot joint 128. This pattern can be repeated as desired such that the suture 180 extends through multiple pivot joints 128 and is wrapped around struts segments between adjacent pivot joints 128. One end of the suture 180 can be knotted inside of the frame (similar to knot 182) at one pivot joint and the other end of the suture 180 can be knotted on the outside of the outer skirt (similar to knot 184) at another pivot joint. In alternative embodiments, one or both ends of the suture 180 can be tied off to a strut of the frame.

In certain embodiments, the suture used to form stitches 172 (FIGS. 3 and 4) that secure the inflow edge portion of the inner skirt 72 can extend through the pivot joints 128 (as shown in FIG. 7) along the row of strut segments to which the inflow edge portion of the inner skirt is attached. Similarly, the suture used to form stitches 170 that secure the outflow edge portion of the inner skirt 72 can extend through the pivot joints 128 (as shown in FIG. 7) along the row of strut segments to which the outflow edge portion of the inner skirt is attached. As noted above, in the embodiment of FIGS. 3-4, the scallop line of the leaflets 120 is secured to the inner skirt 72 with separate suture(s). As such, the stitches 170, 172 need not extend through the leaflets 120 as depicted in FIG. 7. If the prosthetic valve includes an outer skirt 70, the stitches 172 can also extend through the outer skirt (similar to FIG. 7) so as to secure the inflow edge portion of the outer skirt to the frame 112. The stitches 170 optionally can extend through the outer skirt so as to secure the outer skirt to the same strut segments to which the outflow edge portion of the inner skirt is attached. The outflow edge portion of the outer skirt 70 can be secured to a row of strut segments with one or more sutures that form whip stitches that wrap around the strut segments and extend through the outer skirt and the pivot joints.

In some embodiments, the outer skirt 70 can be relatively thinner or lighter than the inner skirt 72 or the combined thickness of the inner skirt 72 and the leaflets 120. As such, tensioning of the suture 180 can pull a portion of the outer skirt 70 into the channel 142 without pulling any portion of the inner skirt 72 into the channel 142 or substantially avoiding pulling any portion of the inner skirt 72 into the channel 142.

In other embodiments, tensioning of the suture 180 can pull both a portion of the outer skirt 70 and a portion of the inner skirt 72 into the channel 142 such that the suture 180 extending through the channel 142 is surrounded by such portions of the outer skirt and the inner skirt. As such, the suture 180 extending through the channel 142 can be protected from friction with the surrounding rivet area.

As described below, a prosthetic valve can be assembled using an improved process.

For example, an annular frame can be constructed by connecting a plurality of inner struts (e.g., 124a as shown in FIG. 6A) with a plurality of outer struts (e.g., 124b as shown in FIG. 6B). As described above, the inner struts and the outer struts can overlap each other at a plurality of pivot joints, and the inner struts can be configured to pivot relative to the outer struts at the plurality of pivot joints during radial expansion or compression of the frame.

In certain embodiment, a valvular structure can be attached to an inner skirt. The valvular structure can be configured to permit the flow of blood from an inflow end to an outflow end of the valve and block the flow of blood from the outflow end to the inflow end of the valve. In certain embodiments, the valvular structure can include a plurality of leaflets. Each leaflet can have an inflow edge portion. The inflow edge portions of the leaflets can define an undulating, curved scallop line (see, e.g., FIGS. 1 and 3-5).

As described above, the inner skirt (or the inner skirt and leaflets sub-assembly) can be attached to the frame from an interior side of the frame by passing a suture through the inner skirt and a channel extending through at least one of the pivot joints (see, e.g., FIG. 7).

As illustrated in FIGS. 6A-6C, the channel can be formed by overlapping an inner strut with an outer strut. The inner (or outer) strut can include a projection and the outer (or inner) strut can include an aperture, through which the projection can extend.

As described above, an outer skirt can be attached to the frame from an exterior side of the frame by passing the suture through the outer skirt (see, e.g., FIG. 7). In certain embodiments, the suture can be tensioned so as to pull at least a portion of the outer skirt into the channel such that the suture passing through the channel is surrounded by the portion of the outer skirt (see, e.g., FIG. 7).

In certain embodiments, an outflow edge of the inner skirt can be attached to a first row of strut segments that are located immediately adjacent to the scallop line toward an outflow end of the valve (see e.g., FIGS. 3-4). As described above, the outflow edge of the inner skirt can be attached to this first row of strut segments via stitches, which can form a continuous stitching pass that is substantially parallel to the scallop line when the frame is in a radially expanded configuration.

In certain embodiments, an inflow edge of the inner skirt can extend to and generally align with the inflow end of the frame so that the inflow edge of the inner skirt and the lowest row of strut segments that define the inflow end of the frame can form a plurality of triangular areas (see e.g., FIGS. 3-4).

In other embodiments, the inflow edge of the inner skirt can run along a second row of strut segments that are located immediately adjacent to the scallop line toward the inflow end of the frame such that only cells through which the scallop line traverses are completely covered by the inner skirt.

In certain embodiments, the inflow edge or a portion adjacent to the inflow edge of the inner skirt can be attached to the second row of strut segments via stitches, which can form a continuous stitching pass that is substantially parallel to the scallop line when the frame is in a radially expanded configuration (see e.g., FIGS. 3-4).

Figure 8A:
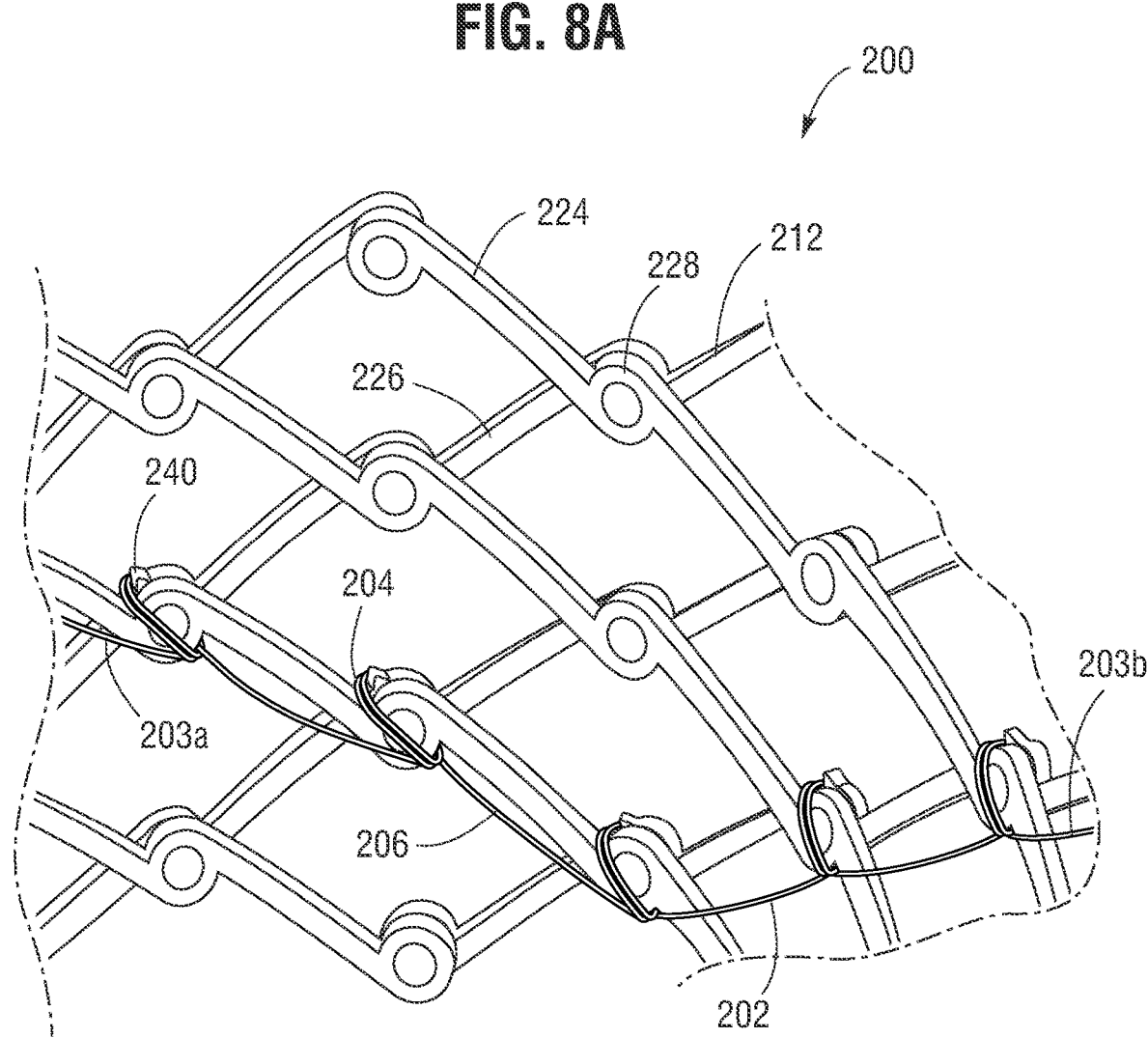
FIG. 8A is an interior view of a portion of a frame in a fully expanded configuration with a leaflet-supporting cord attached to the frame, according to one embodiment.
Figure 8B:
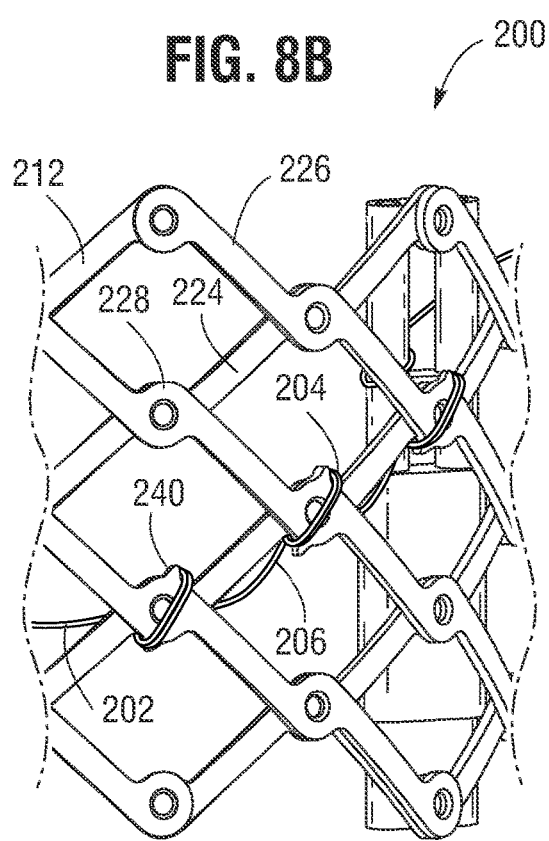
FIG. 8B is an exterior view of the frame depicted in FIG. 8A in the fully expanded configuration.
Figure 8C:
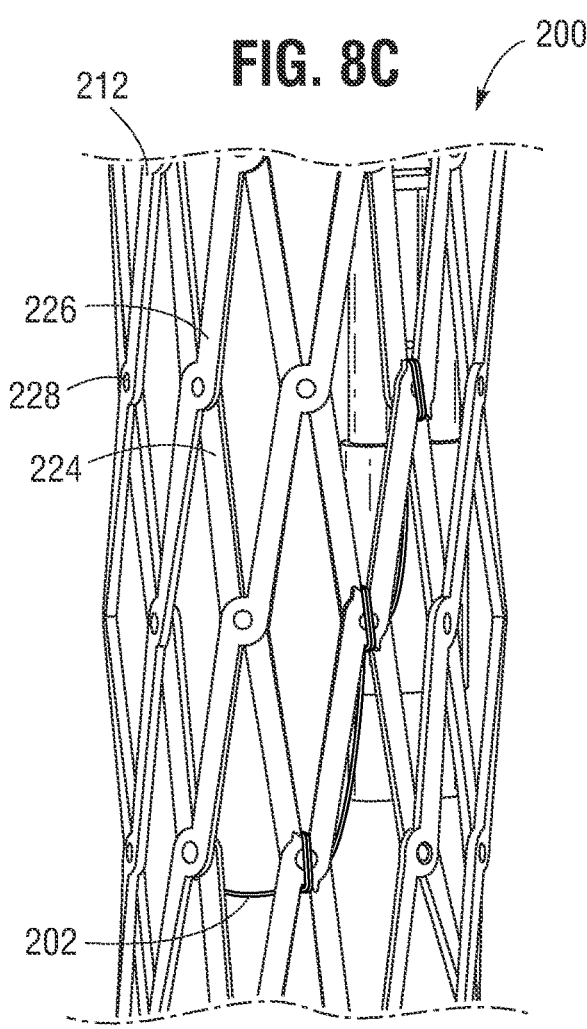
FIG. 8C is an exterior view of the frame depicted in FIG. 8A in a partially compressed configuration.

FIGS. 8A-8C show another embodiment of a prosthetic valve 200. In this embodiment, the prosthetic valve 200 includes an annular frame 212, which includes a plurality of inner struts 224 and a plurality of outer struts 226. The inner struts 224 can overlap adjacent outer struts 226 at a plurality of pivot joints 228. Radial expansion or compression of the frame 212 can cause the inner struts 224 to pivot relative to the outer struts 226 at the pivot joints 228, as previously described.

The prosthetic valve 200 further includes one or more leaflet-supporting cords 202 attached to the frame 212. In some embodiments, the leaflet-supporting cords 202 can be made of a thick suture, such as Ethibond or Dyneem 2-0. In some embodiments, the leaflet-supporting cords 202 can comprise other suture materials, such as a braided, multi-filament suture. In other embodiments, the cords 202 can comprise flexible wires, cables, or strips of fabric. For example, the cords 202 can comprise wires made of metal materials such as stainless steel, cobalt chrome, Nitinol, and the like, or the combination thereof. In another example, the cords 202 can include polymeric material such as polyethylene terephthalate (PET), Dyneema, etc. In some embodiments, the cords 202 can be configured as sutures or strings. In another embodiment, the cords 202 can be configured as a flat, folded or a woven or braided sleeve. The cords 202 can have a thickness or diameter ranging between about 0.01 mm and about 2 mm. In some embodiments, the cords 202 can have a thickness or diameter ranging between about 0.05 mm and about 1 mm. In one specific embodiment, the cords 202 can have a thickness or diameter ranging between about 0.1 mm and about 0.7 mm.

Each leaflet-supporting cord 202 can include a plurality of anchoring portions 204 and a plurality of suspended portions 206. Each suspended portion 206 can extend between two adjacent anchoring portions 204. The anchoring portions 204 can be affixed to respective anchoring features 240 of the frame 212 adjacent the pivot joints 228. Example embodiments of anchoring features 240 are described in more details below.

Figure 8D:
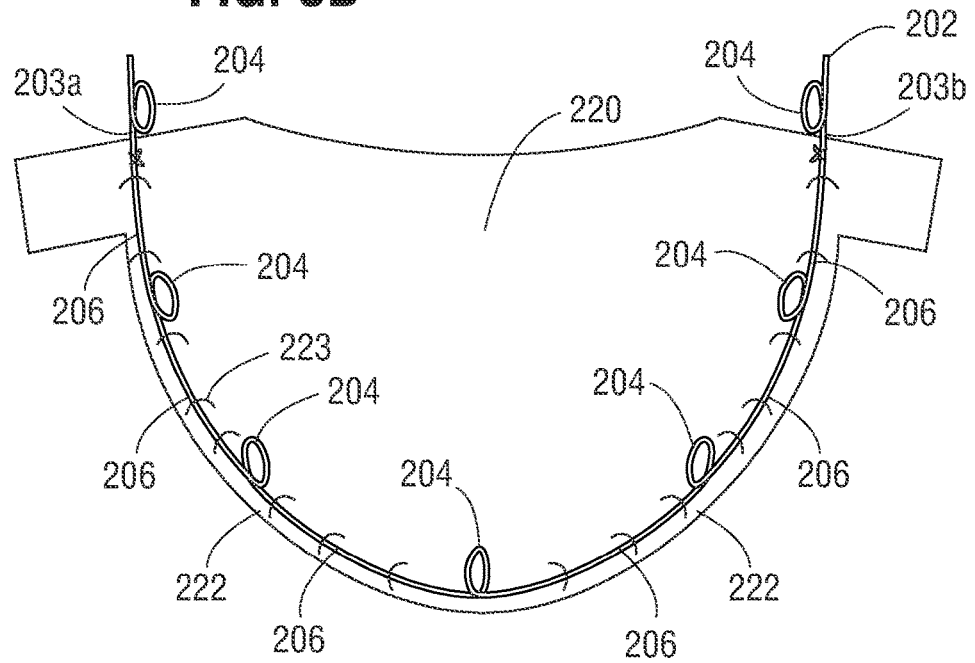
FIG. 8D is a flattened view of a leaflet attached to a leaflet-supporting cord.

The valvular structure of the prosthetic valve 200 can include a plurality of leaflets 220. As shown in FIG. 8D, each leaflet 220 can have a corresponding cusp edge portion 222. The cusp edge portion 222 of each leaflet 220 can be connected to a respective suspended portion 206 of an adjacent leaflet-supporting cord 202, for example, by sutures 223. For example, a single suture can be used to form multiple stitches that extend around the suspended portions 206 of the cord and through the leaflet material along the cusp edge portion of the leaflet. In another example, a single suture can be used to form multiple in-and-out stitches that extend through the suspended portion 206 of the cord and the leaflet material along the cusp edge portion of the leaflet. In another example, multiple sutures can be used to form discrete stitches that extend through or around the suspended portion 206 and the leaflet material along the cusp edge portion of the leaflet. When a thick suture line is used for the leaflet-supporting cord 202, the leaflet-supporting cord 202 itself can serve as a structural component that bears the diastolic loads.

Although not shown in the drawings, the prosthetic valve 200 can include an outer skirt (e.g., outer skirt 70) mounted on the outside of the frame 212. The prosthetic valve 200 can also include an inner skirt mounted on the inside of the frame. If an inner skirt is used, it need not be used for mounting the leaflets to the frame.

As shown in FIGS. 8A-8C, one segment 203*a* of a leaflet-supporting cord 202 can extend diagonally along one of the inner struts 224. Another segment 203*b* of the leaflet-supporting cord 202 can extend diagonally along one of the outer struts 226. The segments 203*a* and 203*b* can extend diagonally along respective inner and outer struts 224, 226 irrespective of the expansion or compression state of the frame 212.

In some embodiments, a single leaflet-supporting cord can be used to connect all of the leaflets to the frame. For example, if the valvular structure has three leaflets 220, the single leaflet-supporting cord 202 can form six interconnected continuous segments. Each pair of two adjacent segments (e.g., 203*a*, 203*b*) can have a plurality of suspended portions 206 that are attached to a corresponding cusp edge portion (e.g., 222) of one of the leaflets.

Alternatively, a plurality of leaflet-supporting cords can be used to connect the plurality of leaflets to the frame. For example, in one embodiment, three leaflets 220 can be respectively connected to the suspended portions 206 of three leaflet-supporting cords 202, wherein each leaflet-supporting cord 202 has two connected segments (e.g., 203*a*, 203*b*). In another embodiment, three leaflets 220 can be respectively connected to the suspended portions 206 of six leaflet-supporting cords 202, wherein each leaflet 220 is connected to a pair of adjacent leaflet-supporting cords 202.

As noted above, each segment (e.g., 203*a*, 203*b*) of the leaflet-supporting cord 202 can extend diagonally along one of the inner struts 224 or outer struts 226. Thus, when attached to the frame 212, the one or more leaflet-supporting cords 202 can form an undulating, curved loop that extend along the cusp edge portions 222 of the leaflets. Because the one or more leaflet-supporting cords 202 are attached to the frame 212 at discrete anchoring portions 204, the suspended portions 206 can support the leaflets 220 between the anchoring portions 204, in a manner similar to a hammock.

FIGS. 9A-9C show some exemplary embodiments of a pivot joint 228 of the frame 212.

In FIG. 9A, an inner strut 224 and an outer strut 226 are pivotably coupled to each other at a pivot joint 228a. In this example, the inner strut 224 has an enlarged intermediate segment 230 which interconnects two linear strut segments 232, which are offset to each other and located on opposite side of the intermediate strut segment 230. Likewise, the outer strut 226 has an enlarged intermediate segment 234 which interconnects two linear strut segments 236, which are offset to each other and located on opposite side of the intermediate strut segment 234. The inner strut 224 and the outer strut 226 can be pivotably coupled to each other by a pivot member 238 (e.g., a rivet or pin) extending through the geometric center of the intermediate strut segments 230, 234.

In this example, the intermediate strut segment 230 of the inner strut 224 has an opening 242, which is spaced apart from the pivot member 238 and located adjacent one of the linear strut segments 232. In some embodiments, the opening 242 can be positioned so that the outer strut 226 does not cover the opening 242 regardless of the angle between the inner strut 224 and the outer strut 224 at the pivot joint 228a during the radial expansion or compression of the frame.

FIG. 9B shows another embodiment of a pivot joint 228b formed by the inner strut 224 and the outer strut 224. In this example, the intermediate strut segment 230 of the inner strut 224 has two openings 242a, 242b, which are spaced apart from the hinge 238 and located at diametrically opposing locations of the pivot joint 228b. In some embodiments, the openings 242a, 242b can be positioned so that the outer strut 226 does not cover any of the openings 242a, 242b regardless of the angle between the inner strut 224 and the outer strut 226 at the pivot joint 228b during the radial expansion or compression of the frame.

FIG. 9C shows yet another embodiment of a pivot joint 228c formed by the inner strut 224 and the outer strut 226. Similarly, the pivot joint 228c has two openings 242c and 242d, which are spaced apart from the hinge 238 and located at diametrically opposing locations of the pivot joint 228c. In this example, the inner strut 224 has a pair of junctional areas 231a, 231b between the intermediate strut segment 230 and the opposing linear strut segments 232. The openings 242c, 242d are located at the respective junctional areas 231a, 231b. In some embodiments, the junctional areas 231a, 231b can be positioned so that the outer strut 226 does not cover any of the openings 242c, 242d regardless of the angle between the inner strut 224 and the outer strut 226 at the pivot joint 228c during the radial expansion or compression of the frame.

Figure 9D:
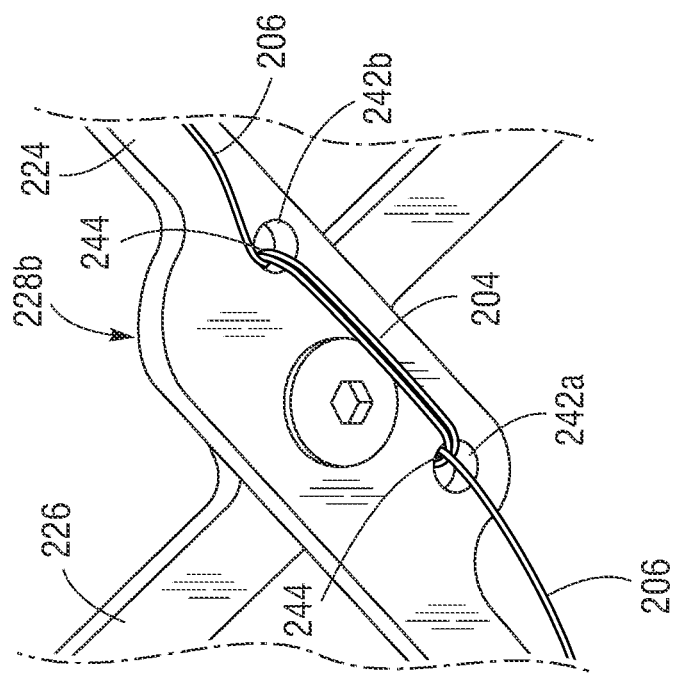
FIG. 9D is a perspective view of the pivot joint depicted in FIG. 9A with a leaflet-supporting cord extending through the opening, according to one embodiment.
Figure 9E:
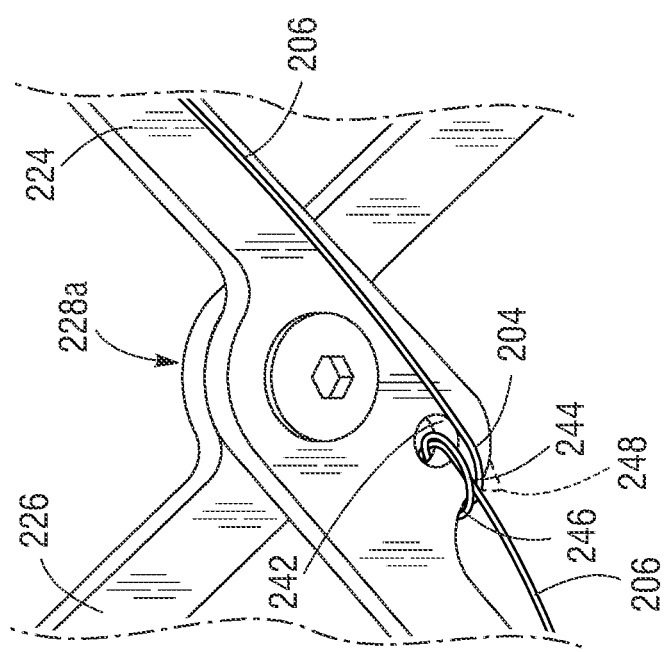
FIG. 9E is a perspective view of the pivot joint depicted in FIG. 9B with a leaflet-supporting cord extending through the two openings, according to one embodiment.

Any of the openings (242, 242a-d) described above can constitute a part of the anchoring feature 240 for supporting the leaflet-supporting cords 202 on the frame. For example, FIG. 9D illustrates affixing an anchoring portion 204 of a leaflet-supporting cord 202 to the pivot joint 228a through the opening 242. FIG. 9E illustrates affixing the anchoring portion 204 of the leaflet-supporting cord 202 to the pivot joint 228b through two openings 242a-b.

As shown in FIG. 9D, the anchoring portion 204 of the leaflet-supporting cord 202 can extend through the opening 242 of the pivot joint 228a. Further, the anchoring portion 204 can form one or more loops of the cord extending through the opening 242. For example, in the illustrated embodiment, the anchoring portion 204 extends through the opening 242 and wraps around the intermediate strut segment 230 of the inner strut 224 twice to form double loops around the pivot joint 228a. In alternative embodiments, the anchoring portion 204 can be looped through the opening 242 more than two times.

In some embodiments, the one or more loops of the anchoring portion 204 can include a self-locking knot 244 which can prevent the anchoring portion 204 from sliding relative to the pivot joint 228a, thus reducing the risk of abrasion of the leaflet-supporting cord 202. For example, after the anchoring portion 204 forms one or more loops around the pivot joint 228a, the suspended portion 206 of the leaflet-supporting cord 202 can be threaded through the one or more loops to form the knot 244. Because the suspended portion 206 is attached to one of the leaflets, the knot 244 can be self-tightened by a pulling force applied to the suspended portion 206 during the diastolic phase when the leaflets are stretched by the pressure gradient across the prosthetic valve.

As shown in FIG. 9E, the anchoring portion 204 of the leaflet-supporting cord 202 can extend through both openings 242a-b of the pivot joint 228b and can form one or more loops around the pivot joint 228b. For example, the anchoring portion 204 can extend through both openings 242a-b and wrap around both the intermediate strut segment 230 of the inner strut 224 and the intermediate strut segment 234 of the outer strut 226 twice to form double loops around the pivot joint 228b. In alternative embodiments, the anchoring portion 204 can form more than two loops. Similarly, the one or more loops of the anchoring portion 204 can include a self-locking knot 244 which can prevent the anchoring portion 204 from sliding relative to the pivot joint 228b. Although it is not shown, it should be understood that the same technique for mounting the anchoring portion 204 can also be applied to the pivot joint 228c (FIG. 9C).

Figure 10B:
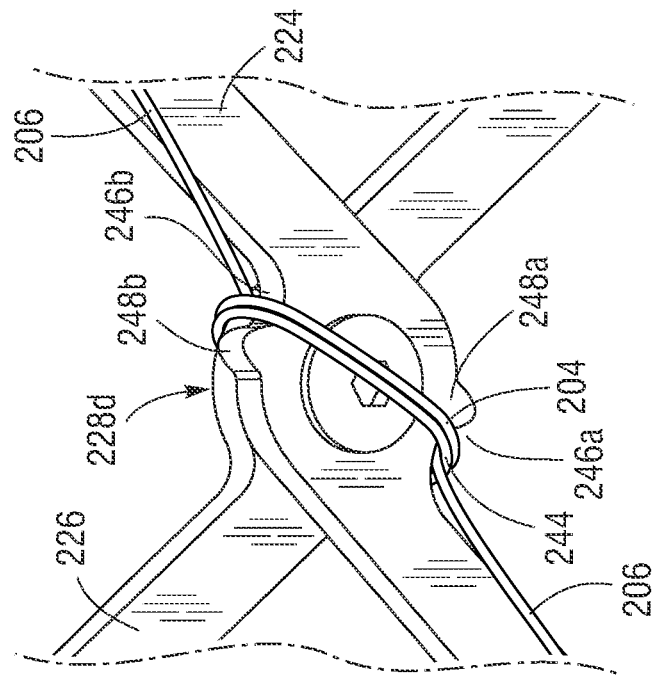
FIG. 10B is a perspective view of the pivot joint depicted in FIG. 10A with a leaflet-supporting cord extending through the two notches, according to one embodiment.
Figure 10A:
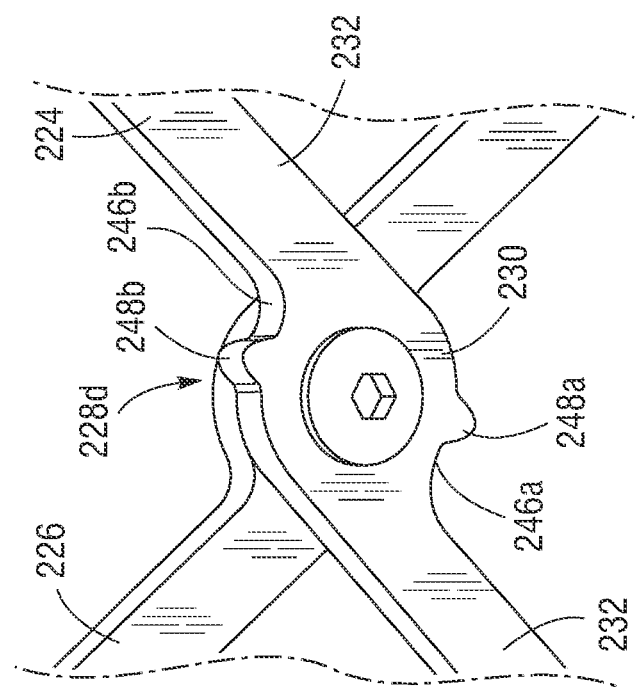
FIG. 10A is a perspective view of a pivot joint having two notches, according to one embodiment.

FIG. 10A shows another embodiment of a pivot joint 228d formed by the inner strut 224 and the outer strut 224. In this example, the pivot joint 228d has two notches 246a, 246b respectively located at the junctional areas between the intermediate strut segment 230 and opposing linear strut segments 232. Specifically, the intermediate strut segment 230 has a pair of bumps or protrusions 248a, 248b protruding from the intermediate strut segment 230. The pair of bumps 248a, 248b desirably are located at diametrically opposing sides of the intermediate strut segment 230. Each notch (246a or 246b) is formed between a corresponding bump (248a or 248b) and its adjacent linear strut segment 232.

The notches 246a, 246b can also constitute a part of the anchoring feature 240 for affixing the anchoring portion 204 of the leaflet-supporting cords 202 to the pivot joint 228d. As shown in FIG. 10B, the anchoring portion 204 of the leaflet-supporting cord 202 can extend through both notches 246a, 246b, and wrap around both the intermediate strut segment 230 of the inner strut 224 and the intermediate strut segment 234 of the outer strut 226 to form one or more loops. Similarly, the one or more loops of the anchoring portion 204 can include a self-locking knot 244 which can prevent the anchoring portion 204 from sliding relative to the pivot joint 228d.

It should be noted that the anchoring features depicted in FIGS. 9A-9E and 10A-10B are merely illustrative and not limiting. For example, although the openings 242, 242a, 242b, 242c and 242d described above are located on the inner strut 224, it should be understood that, in some embodiments, those openings can be located on the outer strut 226 such that the inner strut 224 does not cover any of the openings regardless of the angle between the inner strut 224 and the outer strut 226 during the radial expansion or compression of the frame.

In other embodiments, when a pair of openings (e.g., 242a and 242b, or 242c and 242d) are used, one of the openings can be located on the inner strut 224 and the other opening can be located on the outer strut 226. In some embodiments, those openings can be so positioned that the outer strut 226 does not cover the opening on the inner strut 224 and the inner strut 224 does not cover the opening on the outer strut 226 irrespective of the angle between the inner strut 224 and the outer strut 226 during the radial expansion or compression of the frame.

Yet in another embodiment, the anchoring features can include both an opening and a notch. For example, the pivot joint 228a depicted in FIG. 9D can include not only the opening 242, but also a notch 246 adjacent a bump or protrusion 248 (shown in dashes in FIG. 9D) located at an adjacent junctional area between the intermediate strut segment 230 and the linear strut segment 232. Thus, the anchoring portion 204 of the leaflet-supporting cord 202 can extend through both the opening 242 and the notch 246, and loop around the intermediate strut segment 230 for a more secured affixation to the pivot joint 228a.

Although not shown, it should be understood that the anchoring features can include any other means, such as clip(s), hook(s), buckle(s), fastener(s), glue, etc., for affixing the anchoring portion of the leaflet-supporting cords to the pivot joint.

Figure 11A:
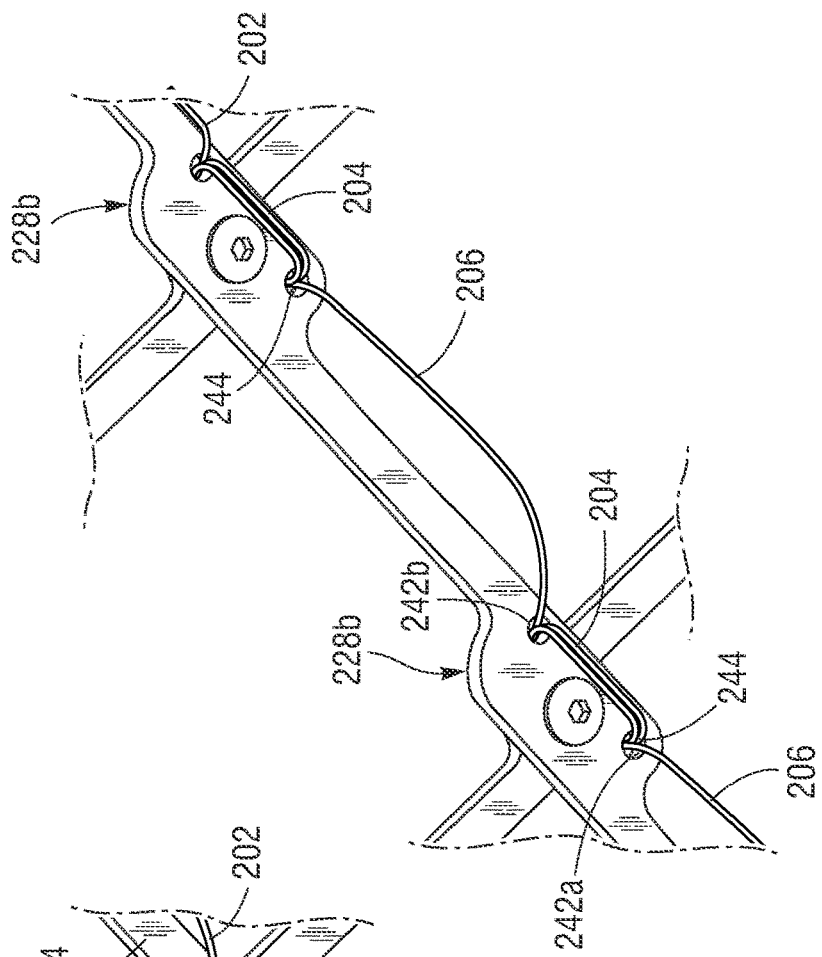
FIG. 11A is a perspective view of one strut having a plurality of notches and a leaflet-supporting cord attached to the strut through the notches, according to one embodiment.
Figure 11B:
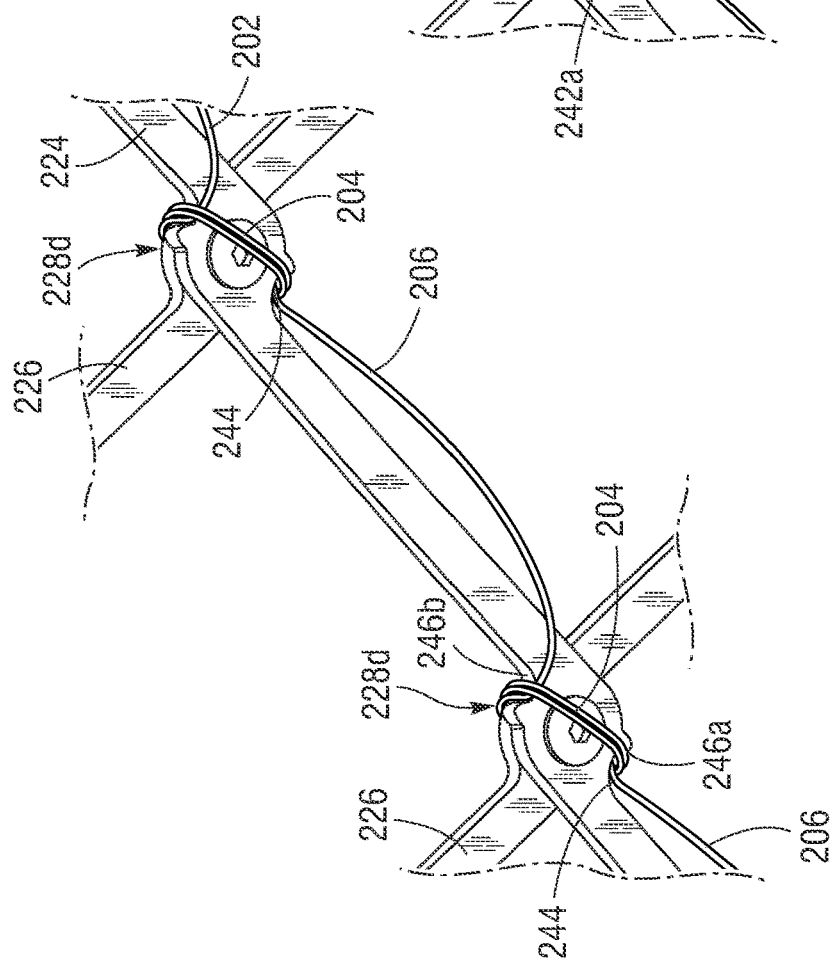
FIG. 11B is a perspective view of one strut having a plurality of openings and a leaflet-supporting cord attached to the strut through the openings, according to one embodiment.

FIGS. 11A-11B depict two examples of attaching a leaflet-supporting cord 202 to an inner strut 224. In FIG. 11A, the inner strut 224 overlaps with outer struts 226 at a plurality of pivot joints 228d, each of which has two notches 246a-b. The anchoring portions 204 of the leaflet-supporting cord 202 in the illustrated embodiment are affixed to pivot joints 228d by looping through the respective notches 246a-b and forming self-tightening knots 244. In FIG. 11B, the inner strut 224 overlaps with outer struts 226 at a plurality of pivot joints 228b, each of which has two openings 242a-b. The anchoring portions 204 of the leaflet-supporting cord 202 are affixed to pivot joints 228b by looping through the respective openings 242a-b with self-tightening knots 244.

In both examples, the suspended portion 206 of the leaflet-supporting cord 202 hangs between adjacent anchoring portions 204. The path of the anchoring portions 204 at the pivot joints (228d or 228b) and the direction of the suspended portion 206 can generally align with the longitudinal axis of the inner strut 224.

The prosthetic valve 200 can be assembled in several steps. In an example embodiment, an annular frame 212 can be formed by connecting a plurality of inner struts 224 with a plurality of outer struts 226 at a plurality of pivot joints 228. As noted above, the plurality of inner struts 224 can be configured to pivot relative to the plurality of outer struts 226 at the plurality of pivot joints 228 during radial expansion or compression of the frame 212. One or more leaflet-support cords 202 can then be attached to the frame 212 such that each cord 202 extends along one of inner struts 224 or outer struts 226 at spaced apart locations. A plurality of leaflets 220 can be attached to the one or more leaflet-support cords 202, such as shown in FIG. 8D.

As noted above with reference to FIGS. 8A-8C, each of the one or more leaflet-supporting cords 202 can include at least a first segment 203a and a second segment 203b. Attaching the one or more leaflet-supporting cords 202 to the frame 212 can include extending the first segment 203a diagonally along one of the inner or outer struts along a diagonal line or path extending from the outflow end of the frame to the inflow end of the frame and extending the second segment 203b diagonally along another one of the inner or outer struts along a diagonal line or path extending from the inflow end of the frame to the outflow end of the frame.

In some embodiments, the plurality of leaflets 220 can be attached to a single continuous cord 202 that extends along the entire circumference of the frame through 360 degrees. In some embodiments, the plurality of leaflets 220 can be attached to a plurality of respective separate leaflet-supporting cords 202.

In some embodiments, the one or more leaflet-supporting cords 202 can be attached to the frame 212 by affixing anchoring portions 204 of the leaflet-supporting cords 202 to respective anchoring features 240 of the frame 212 adjacent the pivot joints 228.

In some embodiments, affixing the anchoring portions 204 to respective anchoring features 240 of the frame 212 can include extending the one or more leaflet-supporting cords 202 through openings (e.g., 242, 242a-d) located in one or both of the inner and outer struts 224, 226.

In some embodiments, affixing the anchoring portions 204 to respective anchoring features 240 of the frame 212 can include extending the one or more leaflet-supporting cords 202 through notches (e.g., 246a-b) located in one or both of the inner and outer struts, 224, 226.

In some embodiments, affixing the anchoring portions 204 to respective anchoring features 240 of the frame 212 can include forming one or more loops at a respective pivot joint 228 by extending the corresponding leaflet-support cord 202 through at least one anchoring feature 240 and around a pair of inner and outer struts 224, 226 at the respective pivot joint 228.

In some embodiments, affixing the anchoring portions 204 to respective anchoring features 240 of the frame 212 can include forming a self-locking knot 244 at the one or more loops.

Figure 12:
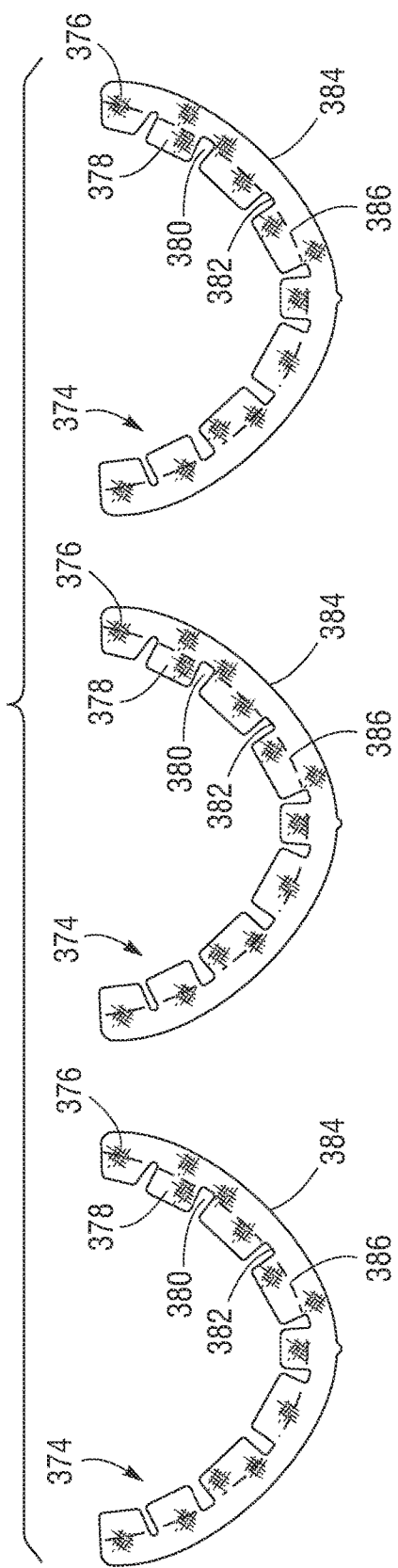
FIG. 12 is a flattened view of three sections of an inner skirt, according to one embodiment.
Figure 13:
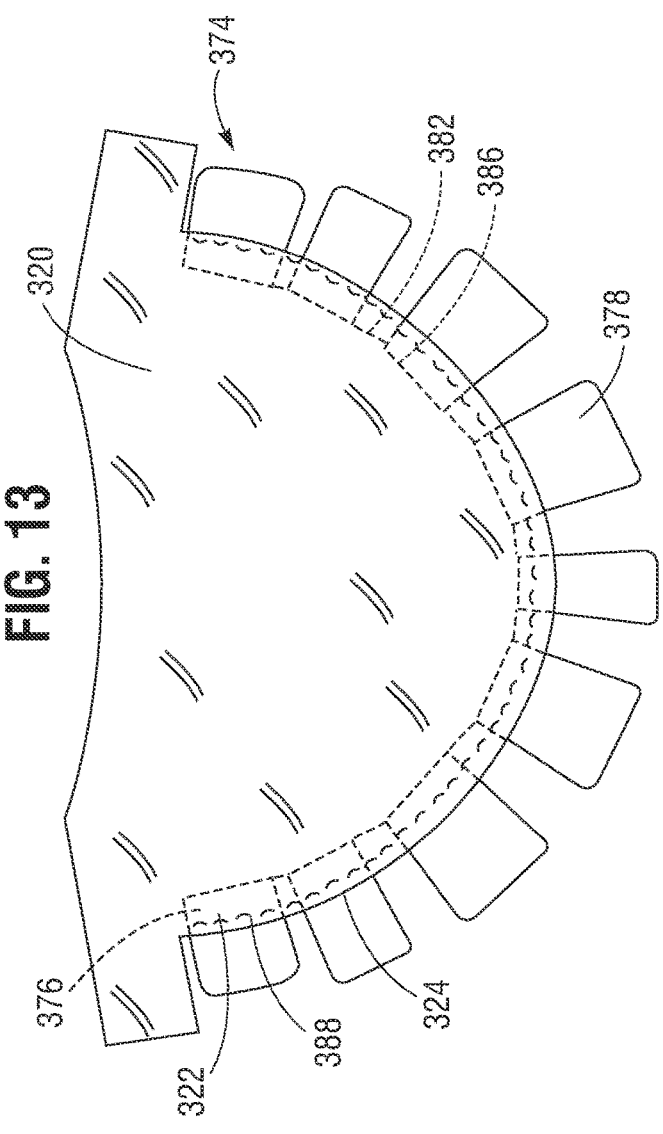
FIG. 13 is a flattened view of a leaflet being attached to one section of the inner skirt depicted in FIG. 12, according to one embodiment.

FIG. 12 shows a flattened view of multiple sections 374 of an inner skirt 372 for a frame, according to one embodiment. FIG. 13 shows a flattened view of a leaflet 320 being attached to a respective section 374 of the inner skirt 372. For a prosthetic valve having a plurality of leaflets 320, the inner skirt 372 can include a plurality of sections 374 (e.g., three sections are shown in FIG. 12) such that each leaflet 320 can be attached to a corresponding section 374. When the plurality of leaflets 320 are mounted to the interior of the frame, the plurality of sections 374 of the leaflet 372 can form an annular shape and collectively form the inner skirt 372, which covers at least a portion of an inner surface of the frame. In the embodiment depicted in FIG. 12, the plurality of sections 374 of the inner skirt 372 are shown as separate pieces of material (e.g., fabric, such as PET fabric) that are unconnected to each other. In other embodiments, the plurality of sections 374 of the inner skirt 372 can form a continuous, unitary piece of material (e.g., fabric, such as PET fabric).

As shown in FIG. 12, each section 374 of the inner skirt 372 can include an undulating, curved support portion 376 and a plurality of flaps 378 extending from the support portion 376. The plurality of flaps 378 can be separated by a plurality of slits 380, each of which separates two adjacent flaps 378. The support portion 376 can be a narrow strip of fabric or natural tissue. The flaps 378 can also be made of fabric or natural tissue. In other illustrated embodiment, at least each section 374 is formed from a unitary piece of material. In other embodiments, the support portion 376 and flaps 378 of a section can be separately formed and subsequently attached to each other, such as by sutures.

In the depicted embodiment, the support portion 376 has a concave first side 382, from which the flaps 378 extend, and a convex second side 384 which is opposite the first side 382. Each flap 378 is connect to the support portion 376 at its base 386, which is along the first side 382, and each slit 380 can extend to the base 386 of the adjacent flaps 378. In certain embodiments, the convex side 384 of the support portion 376 can generally track the curvature of the cusp edge 324 of the leaflet 320.

The support portion 376 can be attached to the cusp edge portion 322 of a leaflet 320, for example, by means of sutures 388. After attaching the support portion 376 to the cusp edge portion 322, the flaps 378 initially can extend inwardly relative to the cusp edge 324 of the leaflet 320 (i.e., the flaps 378 point toward the center of and substantially overlap with the leaflet 320). The flaps 378 can then be folded backward along respective bases 386 such that the folded flaps 378 extend outwardly relative to the cusp edge 324 of the leaflet 320 (i.e., the flaps 378 point away from the center of the leaflet 320 and at least portions of the flaps 378 do not overlap with the leaflet 320), as depicted in FIG. 13. Thus, after mounting the leaflet 320 to the frame, the outwardly extending flaps 378 can generally extend toward the inflow end of the frame.

In other embodiments (not shown), the flaps 378 can extend from the convex second side 384 of the support portion 376. When the support portion 376 is sutured to the cusp edge portion 322 of the leaflet 320, the flaps 378 are not folded and they extend outwardly relative to the cusp edge 324 of the leaflet 320.

FIG. 14 illustrates a method for attaching the inner skirt 372 to a frame 312, according to one embodiment. In this example, the support portion 376 of the inner skirt 372 is attached to the cusp edge portion 322 of the leaflet 320 via a suture 388. Optionally, a reinforcement member 390, such as a strip of high-strength fabric or a suture (e.g., an Ethibond suture), can also be attached to the cusp edge portion 322 of the leaflet 320 via the suture 388 such that the cusp edge portion 322 is sandwiched between the support portion 376 and the reinforcement member 390. The suture 388 can form a plurality of in-and-out stitches that extend along and through the cusp edge portion 322 and the support portion 376, and optionally through or around the reinforcement member 390.

In the example of FIG. 14, the cusp edge portion 322 of the leaflet extends upwardly toward the outflow end of the frame such that a concave region is formed along the outflow surface of the leaflet between the cusp edge portion 322 and the main articulating portion of the leaflet (sometimes referred to as the "belly" of the leaflet). In other examples, the cusp edge portion 322 of the leaflet can turn downwardly and extend toward inflow end of the frame but otherwise can be secured to the inner skirt 372 and optionally the reinforcement member 390 in the same manner as described above.

As shown in FIG. 14, the flaps 378 can extend outside of the frame 312 through adjacent open cells 336 of the frame 312. The flaps 378 extending outside of the frame 312 can extend toward the outflow end of the frame and can overlap adjacent pivot joints 328 of the frame 312 above the scallop line (suture 388). The pivot joint 328 can be any type of the pivot joints described herein. Further, the flaps 378 extending outside of the frame 312 can be attached to an outer skirt 370, for example, via another suture 392. In some embodiments, the suture 392 can tie the outer skirt 370, the flaps 378, and the pivot joint 328 together. In alternative embodiment, the flaps can be folded toward the inflow end of the frame and overlap adjacent pivot joints 328 below the scallop line (suture 388).

FIG. 15 illustrates a method for attaching the inner skirt 320 to the frame 312, according to another embodiment. Similarly, the support portion 376 of the inner skirt 372 can be attached to the cusp edge portion 322 of the leaflet 320 (the dashed line 324 indicates the cusp edge of the leaflet 320) as previously described. The flaps 378 can extend outside of the frame 312 into adjacent open cells 336 of the frame 312. In this example, instead of overlapping the adjacent pivot joints 328 as shown in FIG. 14, the flaps 378 are positioned in the middle of the frame cells 336, and directly connected to the outer skirt 370, e.g., by means of sutures. In this example, the flaps 378 can reside between the inner circumference of the frame (defined by the inner struts) and the outer circumference of the frame (defined by the outer struts). However, in other examples, the outer skirt (which can have a relatively tight or snug fit around the outer surface of the frame when the frame is radially expanded), can support the flaps outside of the frame.

The embodiments illustrated in FIGS. 14-15 allow secure attachment of the leaflets 320 to the frame 312 in a structural load bearing connection. Traditionally, leaflet attachment is achieved by attaching the leaflet to an inner skirt which is in turn attached to the frame. By attaching the leaflets 320 to the inner skirt 372, which is directly connected to the outer skirt 370, several advantages can be achieved. For example, a load can be transferred from the inner skirt 372 to the outer skirt 370 which is located outside of the frame 312. Such load transfer may improve blood flow at the connection area between the leaflet and the frame, thus reducing risk of thrombus formation. In addition, leaflet to bare frame contact during cycling is less abrasive (and damaging) to a leaflet when compared to a leaflet's contact with a conventional inner skirt. In particular, by extending flaps 378 of the inner skirt 372 to the exterior of the frame 312 (through frame cells 336) or at least into the frame cells 336 spaced from an inner circumference of the frame, the portion of the inner skirt 372 remaining interior of the frame (e.g., the support portion 376) is reduced and can improve valve durability. Further, compared with a conventional skirt, the amount of material needed to form the skirt is substantially reduced and the inner skirt need not be connected to individual struts of the frame, thus decreasing the overall crimp profile of the prosthetic and reducing the number of parts used for forming valve assembly and the associated assembly time.

In further alternative embodiments, the flaps 378 can extend through the cells 336 of the frame and along the outer surface of the frame, where the flaps can be secured to a circumferential row of strut segments, such as with sutures, and the outer skirt can be optional. For example, the flaps 378 can extend all the way to the outflow end of the frame and can be secured (e.g., with sutures) to the circumferential row of strut segments forming the outflow end of the frame. In such embodiments, the flaps can effectively form an outer skirt that helps seal the prosthetic valve against the surrounding tissue.

In still further alternative embodiments, the cusp edge portions 322 of the leaflets can be attached directly to the outer skirt 370 through the open cells 336 of the frame, without an inner skirt 372.

In yet further alternative embodiments, the flaps 378 of the inner skirt 372 can be attached to the anchoring portions 204 of the leaflet-supporting cords 202 described above, e.g., via sutures. In other words, the suspended portions 206 of the leaflet-supporting cords 202 can not only support the leaflets 220 between the anchoring portions 204, but also support the plurality of flaps of the inner skirt 372.

General Considerations

It should be understood that the disclosed embodiments can be adapted for delivering and implanting prosthetic devices in any of the native annuluses of the heart (e.g., the aortic, pulmonary, mitral, and tricuspid annuluses), and can be used with any of various delivery devices for delivering the prosthetic valve using any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

We claim:

1. A method of assembling a prosthetic valve, the method comprising:
   forming an annular frame by connecting a plurality of inner struts with a plurality of outer struts at a plurality of pivot joints, wherein the plurality of inner struts are configured to pivot relative to the plurality of outer struts at the plurality of pivot joints during radial expansion or compression of the frame;
   attaching one or more leaflet-support cords to the frame such that each cord extends along one of inner or outer struts at spaced apart locations; and
   attaching a plurality of leaflets to the one or more leaflet-support cords.

2. The method of claim 1, wherein each of the one or more leaflet-supporting cords comprises at least a first segment and a second segment, and wherein attaching the one or more leaflet-supporting cords to the frame comprises extending the first segment diagonally along one of the inner or outer struts and extending the second segment diagonally along another one of the inner or outer struts.

3. The method of claim 1, wherein the one or more leaflet-supporting cords comprise a single continuous cord, and wherein attaching the plurality of leaflets to the one or more leaflet-support cords comprises attaching the plurality of leaflets to the single continuous cord.

4. The method of claim 1, wherein the one or more leaflet-supporting cords comprise a plurality of leaflet-supporting cords, and wherein attaching the plurality of leaflets to the one or more leaflet-support cords comprises connecting each of the leaflet-supporting cords to a respective leaflet.

5. The method of claim 1, wherein each of the leaflet-supporting cords comprises a plurality of anchoring portions and a plurality of suspended portions, each suspended portion extending between two adjacent anchoring portions, and wherein attaching the one or more leaflet-supporting cords to the frame comprises affixing the anchoring portions to respective anchoring features of the frame adjacent the pivot joints.

6. The method of claim 5, wherein affixing the anchoring portions to respective anchoring features of the frame comprises extending the one or more leaflet-supporting cords through openings located in one or both of the inner and outer struts.

7. The method of claim 5, wherein affixing the anchoring portions to respective anchoring features of the frame comprises extending the one or more leaflet-supporting cords through notches located in one or both of the inner and outer struts.

8. The method of claim 5, wherein affixing the anchoring portions to respective anchoring features of the frame comprises affixing each of the anchoring portion to a pair of first and second anchoring features of the frame located at diametrically opposing locations of a respective pivot joint.

9. The method of claim 5, wherein affixing the anchoring portions to respective anchoring features of the frame comprises forming one or more loops at a respective pivot joint by extending the corresponding leaflet-support cord through at least one anchoring feature and around a pair of inner and outer struts at the respective pivot joint.

10. The method of claim 9, wherein affixing the anchoring portions to respective anchoring features of the frame comprises forming a self-locking knot at the one or more loops.

11. A method of assembling a prosthetic valve, the method comprising:
providing an annular frame comprising a plurality of interconnected struts, wherein the annular frame is radially compressible and expandable;
attaching a plurality of leaflets to an inner skirt of the prosthetic valve, the leaflets being configured to permit blood flow from an inflow end to an outflow end of the prosthetic valve and block blood flow from the outflow end to the inflow end of the prosthetic valve, wherein the inner skirt comprises a plurality of flaps separated by a plurality of slits;
extending the plurality of flaps through adjacent open cells of the frame; and
attaching the plurality of flaps to an outer skirt of the prosthetic valve,
wherein the plurality of struts are pivotably connected to one another at a plurality of pivot joints such that an axial force applied to the frame causes the plurality of struts to pivot relative to one another about pivot joints, thereby causing the frame to radially expand or compress.

12. The method of claim 11, further comprises folding each flap along a base of the flap so that the flap extends toward the inflow end of the prosthetic valve.

13. The method of claim 11, further comprises overlapping the plurality of flaps with adjacent pivot joints of the frame.

14. The method of claim 11, wherein attaching the plurality of flaps to the outer skirt comprises attaching the plurality of flaps to the outer skirt with sutures.

15. The method of claim 11, the inner skirt comprises a plurality of sections, each of which is attached to a respective leaflet.

16. The method of claim 15, wherein each section comprises a support portion sutured to a cusp edge portion of a respective leaflet, the support portion having a convex edge that corresponds to a shape of the cusp edge portion.

17. The method of claim 16, wherein the flaps extend from a concave edge of each support portion.

18. The method of claim 17, wherein the cusp edge portion of each leaflet is folded toward the outflow end of the prosthetic valve and the flaps extend toward the outflow end of the prosthetic valve.

19. The method of claim 15, wherein the plurality of sections comprise separate pieces of material.

* * * * *